US012290381B2

(12) United States Patent
Brockelman et al.

(10) Patent No.: US 12,290,381 B2
(45) Date of Patent: *May 6, 2025

(54) METHOD AND SYSTEM FOR CAPTURING PATIENT FEEDBACK FOR A MEDICAL TREATMENT

(71) Applicant: MoreBetter, Ltd., Hyattsville, MD (US)

(72) Inventors: Franco Brockelman, Arvada, CO (US); Keenan Keeling, University Park, MD (US); Branden Hall, Hyattsville, MD (US)

(73) Assignee: MoreBetter, Ltd., Hyattsville, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 18/410,076

(22) Filed: Jan. 11, 2024

(65) Prior Publication Data
US 2024/0138761 A1 May 2, 2024

Related U.S. Application Data

(63) Continuation of application No. 17/573,961, filed on Jan. 12, 2022, now Pat. No. 11,883,192, which is a
(Continued)

(51) Int. Cl.
A61B 5/00 (2006.01)
G16H 10/60 (2018.01)
G16H 20/10 (2018.01)

(52) U.S. Cl.
CPC .......... A61B 5/4842 (2013.01); A61B 5/4836 (2013.01); A61B 5/7405 (2013.01);
(Continued)

(58) Field of Classification Search
CPC ... A61B 5/4842; A61B 5/4836; A61B 5/7405; A61B 5/742; A61B 5/746; A61B 5/7475;
(Continued)

(56) References Cited

U.S. PATENT DOCUMENTS

2003/0144580 A1 7/2003 Iliff
2007/0226012 A1* 9/2007 Salgado ............... G16H 15/00
705/3
(Continued)

FOREIGN PATENT DOCUMENTS

JP 2003223507 A * 8/2003
JP 2004005359 A 1/2004
(Continued)

OTHER PUBLICATIONS

Desai, H.; Eschberger, K.; Agrawal, A.; Grant, B.; Murphy, T.F.; et al. "Environmental factors and daily symptoms in patients with chronic obstructive pulmonary disease." American Journal of Respiratory and Critical Care Medicine, suppl. MeetingAbstracts181.1 American Thoracic Society. (May 1, 2010) (Year: 2010).*
(Continued)

Primary Examiner — Linh Giang Le
(74) Attorney, Agent, or Firm — Panitch Schwarze Belisario & Nadel LLP

(57) ABSTRACT

A method for capturing patient feedback for a medical treatment includes: receiving user instructions indicating a symptom being treated, a symptom score for the symptom being treated, and an indication of a beginning of a treatment session; receiving patient feedback comprising an updated symptom score for the symptom being treated and/or absence or presence of one or more of a plurality of attributes; storing the received patient feedback and a time in the treatment session at which the respective patient feedback was received; repeating the receiving of patient
(Continued)

feedback and storage of data during the treatment session; and receiving a user instruction indicating an ending of the treatment session, wherein an alerting module alerts a user of the computing device for input of patient feedback after a predetermined period of time has elapsed following receipt of patient feedback without a subsequent receipt of patient feedback.

20 Claims, 9 Drawing Sheets

Related U.S. Application Data continuation of application No. 16/607,167, filed as application No. PCT/US2018/029561 on Apr. 26, 2018, now Pat. No. 11,253,195.

(60) Provisional application No. 62/490,240, filed on Apr. 26, 2017.

(52) U.S. Cl.
CPC .............. *A61B 5/742* (2013.01); *A61B 5/746* (2013.01); *A61B 5/7475* (2013.01); *G16H 10/60* (2018.01); *G16H 20/10* (2018.01)

(58) Field of Classification Search
CPC ........ G16H 10/60; G16H 20/10; G16H 50/30; G16H 40/20; G16H 10/20; G16H 80/00
See application file for complete search history.

(56) References Cited

U.S. PATENT DOCUMENTS

| | | |
|---|---|---|
| 2010/0265072 A1 | 10/2010 | Goetz et al. |
| 2012/0157793 A1 | 6/2012 | MacDonald |
| 2014/0052465 A1 | 2/2014 | Madan et al. |
| 2015/0343144 A1 | 12/2015 | Altschul et al. |
| 2017/0017127 A1 | 1/2017 | Gan |
| 2021/0030356 A1 | 2/2021 | Brockelman et al. |

FOREIGN PATENT DOCUMENTS

| | | |
|---|---|---|
| JP | 2012130688 A | 7/2012 |
| WO | 03104939 A2 | 12/2003 |

OTHER PUBLICATIONS

International Search Report (PCT/ISA/210) mailed on Aug. 10, 2018, by the Korean Intellectual Property Office as the International Searching Authority for International Application No. PCT/US2018/029561.

Written Opinion (PCT/ISA/237) mailed on Aug. 10, 2018, by the Korean Intellectual Property Office as the International Searching Authority for International Application No. PCT/US2018/029561.

Desai, H. et al., "Environmental factors and daily symptoms in patients with chronic obstructive pulmonary disease", American Journal of Respiratory and Critical Care Medicine, suppl. Meeting Abstracts181.1, American Thoracic Society, May 1, 2010.

Examiner's Report dated Feb. 15, 2023, issued in corresponding Canadian Application No. 3,146,941, 3 pps.

Examination report No. 1, dated Mar. 10, 2023, issued in corresponding Australian Application No. 2018256830, 9 pps.

Examination report No. 2 for standard patent application, dated Jul. 21, 2023, issued in corresponding Australian Application No. 2018256830, 7 pgs.

Examiner Requisition, dated Feb. 2, 2024, issued in corresponding Canadian Application No. 3,146,941, 5 pages.

* cited by examiner

METHOD AND SYSTEM FOR CAPTURING PATIENT FEEDBACK FOR A MEDICAL TREATMENT

FIELD

The present disclosure relates to the capturing of patient feedback for a medical treatment, specifically the tracking of several patient attributes related to medical treatment in real-time following the taking of medication, particularly as related to the specific batch of a medicine being taken.

BACKGROUND

As modern medicine continues to advance, more and more is learned about the effect that various medicine has on the human body on both a physical and mental level. However, even with everything that has been learned, there is still a lot that is unknown about medicine and how a patient may react. In many instances, each individual may have a different physiological reaction to a medication, such as in terms of allergies, its physical effect on symptoms and other ailments, its effect on the mental state of the patient, etc. In some cases, one patient may react drastically different to a medicine than another patient, which may result in difficulties when attempting to prescribe a new or alternative medication to a patient.

In some instances, a medical professional may prescribe a medicine to a patient and ask them to record effects of the medicine in a journal or other format for later review by the medical professional. To assist patients in the recording of such information, some application programs on computing devices have been developed to enable patients to record feedback. However, existing offerings amount to little more than electronic journals, where the effectiveness is determined solely on the participation of the patient. In other words, the application programs do no more than provide an electronic system for entry of the data, and relies on the patient to provide all of the data.

In addition, current offerings often provide very little capacity in terms of collecting data about the medication itself. With some medications, particularly cannabis and other naturally occurring pharmacological plants (and other materials), the physical and chemical properties can vary greatly from not only strain to strain, but batch to batch due to often complex interplay between environmental and genetic factors. Existing methods for assisting patients in capturing feedback do not go beyond capturing the name of a strain, without regards to any properties of that strain or of the particular batch of the medicine, which can have a significant effect on the patient's reaction to such medicine.

Thus, current offerings related to the capturing of patient feedback not only fail to assist in the capturing of feedback during treatment, but also fail in capturing data regarding the medication being used itself. As such, the current methods for capturing patient feedback amount to little more than electronic means for storing what has traditionally been performed by hand by patients. Thus, there is a need for a technical solution to improve the capturing of patient feedback in real time with respect to medical treatment, as well as the capturing of detailed properties of medicine for use in analyzing the effect of certain chemical properties on an individual patient as well as recommending alternative or future treatment options to the patient.

SUMMARY

The present disclosure provides a description of systems and methods for the capturing of patient feedback for a medical treatment. In one embodiment, a computing device is used by a patient that is specifically configured to capture feedback from the patient with regard to a medical treatment in real-time. Feedback is captured in the form of levels with respect to a particular symptom, as well as other attributes that are experienced by the patient over the course of treatment, with prompts being made to the patient when feedback is not provided during a predetermined period of time during the treatment session, which results in a complete record of care in real-time during such a session. Such methods provide both a more comprehensive capturing of the effectiveness of a treatment for the patient themselves as well as medical professionals, but also a beneficial accounting of the effect of various treatments and medicines on the patient to assist the patient in future treatment of symptoms and other ailments.

A method for capturing patient feedback for a medical treatment includes: receiving, by an input device interfaced with a computing device, a plurality of user instructions indicating at least a symptom being treated, a symptom score for the symptom being treated, and an indication of a beginning of a treatment session; receiving, by the input device interfaced with the computing device, patient feedback comprising at least one of: an updated symptom score for the symptom being treated and absence or presence of one or more of a plurality of attributes; executing, by a querying module of the computing device, a query on a memory of the computing device to store, in the memory of the computing device, the received patient feedback and a time in the treatment session at which the respective patient feedback was received; repeating the receiving of patient feedback and executing steps one or more times during the treatment session; and receiving, by the input device interfaced with the computing device, a user instruction indicating an ending of the treatment session, wherein an alerting module of the computing device is configured to alert a user of the computing device for input of patient feedback after a predetermined period of time has elapsed following receipt of patient feedback without a subsequent receipt of patient feedback.

A system for capturing patient feedback for a medical treatment includes: an alerting module of a computing device; an input device interfaced with the computing device configured to receive a plurality of user instructions indicating at least a symptom being treated, a symptom score for the symptom being treated, and an indication of a beginning of a treatment session, and receive patient feedback comprising at least one of: an updated symptom score for the symptom being treated and absence or presence of one or more of a plurality of attributes; and a querying module of the computing device configured to execute a query on a memory of the computing device to store, in the memory of the computing device, the received patient feedback and a time in the treatment session at which the respective patient feedback was received, wherein the receiving device and querying module are configured to repeat the receiving of patient feedback and execution of queries one or more times during the treatment session, the input device interfaced with the computing device is further configured to receive a user instruction indicating an ending of the treatment session, and the alerting module of the computing device is configured to alert a user of the computing device for input of patient feedback after a predetermined period of time has elapsed following receipt of patient feedback without a subsequent receipt of patient feedback.

BRIEF DESCRIPTION OF THE DRAWING FIGURES

The scope of the present disclosure is best understood from the following detailed description of exemplary embodiments when read in conjunction with the accompanying drawings. Included in the drawings are the following figures.

Further areas of applicability of the present disclosure will become apparent from the detailed description provided hereinafter. It should be understood that the detailed description of exemplary embodiments are intended for illustration purposes only and are, therefore, not intended to necessarily limit the scope of the disclosure.

DETAILED DESCRIPTION

Figure 1:
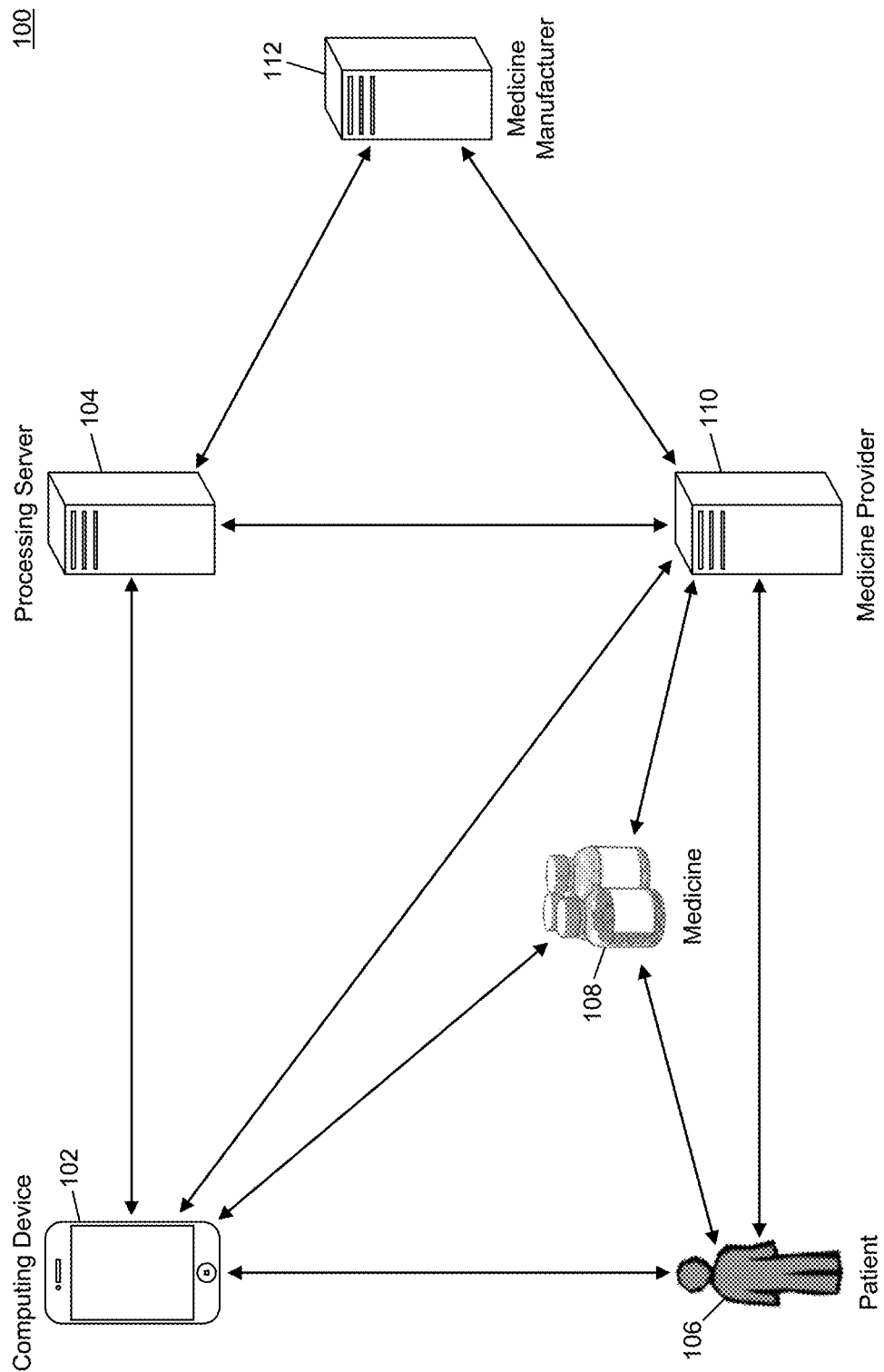
FIG. 1 is a block diagram illustrating a high level system architecture for the capturing of patient feedback for a medical treatment in accordance with exemplary embodiments.

System for Capturing of Patient Feedback and Recommendations for Medical Treatment FIG. 1 illustrates a system 100 for the capturing of patient feedback in real-time for a medical treatment and the identification of recommended medicines for use in medical treatment based on captured patient feedback and associated medicinal properties.

The system 100 may include a computing device 102. The computing device 102, discussed in more detail below, may be configured to capture patient feedback with respect to medical treatment in real-time from a patient 106. The system 100 may also include a processing server 104. The processing server 104, discussed in more detail below, may be configured to identify recommendations with respect to medical treatment for the patient 106 based on previously captured feedback. As discussed herein, the computing device 102 may be used for the capturing of patient feedback while the processing server 104 may be used for the identification of recommendations. However, as will be apparent to persons having skill in the relevant art, in some embodiments the functions performed by the computing device 102 and processing server 104 may be performed by either and/or both devices, such as use of the computing device 102 to identify or assist in the identification of recommendations with respect to medical treatment based on captured patient feedback.

In the system 100, the patient 106 may use a medicine 108 for the treatment of one or more symptoms. The medicine 108 may be any type of medication used in the treatment of symptoms by patients 106. In an exemplary embodiment, the medicine 108 may be cannabis that is prescribed to the patient 106 or otherwise obtained by the patient 106 for use in treating symptoms. With respect to the capturing of patient feedback, the patient 106 may utilize the computing device 102 to record feedback regarding use of the medicine 108 as part of a treatment session. The computing device 102, discussed in more detail below, may be any type of computing device that is specifically configured to perform the functions discussed herein, such as a specifically configured cellular phone, smart phone, smart watch, wearable computing device, implantable computing device, tablet computer, notebook computer, laptop computer, desktop computer, smart television, etc.

The patient 106 may use the computing device 102 and input instructions into the computing device 102 to begin the recording of feedback for a treatment session. As part of the initiation of the treatment session, the patient 106 may supply data that at least indicates one or more symptoms being treated, a symptom score for each symptom, and an indication that the treatment session is starting. The symptom score may be a value (e.g., a number on a scale of 1 to 10) representing the strength of the symptom when the treatment session is beginning. For instance, the patient 106 may select "anxiety" as a symptom and provide a symptom score of 8, indicating that the patient 106 is attempting to treat their anxiety, which they are feeling very strongly (e.g., at an 8 out of a possible 10) as they begin their treatment session.

In some embodiments, the computing device 102 may be configured to capture additional data before a treatment session begins. Such data may include, for instance, data associated with the delivery method of the medicine 108. For example, the patient 106 may indicate the delivery method of the medicine 108 itself (e.g., drops, edibles, vaporization, inhalation, etc.) as well as an amount related to the delivery method. In cases where the medicine may be consumed throughout the treatment session (e.g., repeated inhalations), the computing device 102 may be configured provide an interface to the patient 106 to indicate such consumption during the course of the treatment session, for capturing by the computing device 102. For example, if the patient 106 is smoking cannabis as the medicine 108 and delivery method, the patient 106 may indicate throughout the treatment session when they inhale the cannabis and for how long, where the computing device 102 may capture such data and record it as part of the treatment session. In such instances, the computing device 102 may capture the dosage and consumption along with a timestamp indicating the time at which the consumption occurred.

In some cases, the additional data may also include data associated with the medicine 108 itself. Such data may include, for example, physical or chemical properties of the medicine 108, data associated with the manufacture of the medicine 108, etc. Physical or chemical properties of the medicine 108 may be dependent on the type of medicine. For instance, cannabis may have different physical and chemical properties for capture than ibuprofen. Physical properties for cannabis may include, for example, color, smell, texture, seed size, etc. Chemical properties for cannabis may include chemotype, percentages or portions of tetrahydrocannabinol, cannabidiol, cannabinol, cannabinoids, terpenes, etc. In these cases, the properties may be manually entered into the computing device 102 by the patient 106, or received by the computing device 102 via one or more alternative methods.

For instance, the patient 106 may procure the medicine 108 from a medicine provider 110, such as a pharmacy, dispensary, physician, etc. In such instances, the computing device 102 may receive the data from an electronic transmission from a computing system of the medicine provider 110. For example, the computing device 102 may establish a near field communication channel with the medicine provider 110 and receive the data from the medicine provider 110. In another example, the medicine 108 may be packaged with a machine-readable code (e.g., a bar code, quick response (QR) code, etc.) that is encoded with the data. In yet another example, the medicine 108 may be packaged with a machine-readable code that is encoded with a unique identifier associated with the medicine 108 that may be used by the computing device 102 to obtain the data. For instance, the unique identifier may be a batch identifier that identifies the batch from which the medicine 108 was produced, which the computing device 102 may provide to a third party system to obtain the physical and chemical property data therefrom. In one such example, a medicine manufacturer 112 may manufacture or otherwise produce the medicine 108, which may be provided to the medicine provider 110 for sale or distribution to the patient 106. The computing device 102 may provide the batch identifier to the medicine manufacturer 112, either directly or via an intermediate system, such as the medicine provider 110 or processing server 104, where the medicine manufacturer 112 may provide the physical and chemical property data in response thereto.

In some cases, the physical data associated with the medicine 108 may include data related to the storage, manufacturer, and/or distribution of the medicine 108. For instance, the data may further include conditions related to the growing of the medicine 108 (e.g., geographic location, humidity, temperature, pressure, lighting type, lighting intensity, etc.), storage of the medicine 108 (e.g., light level, temperature, etc.), distribution of the medicine 108 (e.g., time and/or date of growth, harvest, manufacture, departure from medicine manufacturer 112, arrival at medicine provider 110, etc.), etc. Such data may be provided to or otherwise captured by the computing device 102 and stored along with the patient feedback related to the treatment session. In cases where the medicine 108 may be used for more than one treatment session, the computing device 102 may be configured to store the data for the medicine 108 for later recall by the patient 106 for use in future treatment sessions. In such cases, the patient 106 may indicate, when starting a treatment session or ending a treatment session, if they run out of the medicine 108.

Once the data is captured and treatment session initiated, the computing device 102 may be configured to capture data from the patient 106 with regards to the treatment of their symptom and other attributes during the course of the treatment session. During the treatment session, the patient 106 may, using a suitable input device of the computing device 102, input patient feedback. The patient feedback may include at least one of: an updated symptom score for one or more of the symptoms being treated, and the absence or presence of one or more of a plurality of attributes related to the medical treatment. The attributes may be related to physiological status of the patient 106 in addition to, or alternative to, the symptom(s) entered at the start of the treatment session, such as feelings, side effects, thoughts, etc. Attributes may include, for example, tired, hungry, nauseous, sore, nervous, anxious, dry mouth, thirsty, itchy, headache, rash, etc. In some cases, attributes and symptoms may include similar, or the same, values (e.g., the patient 106 may start a session to treat anxiety, but may also indicate anxiety as an attribute during a session treating a different symptom).

The computing device 102 may receive the patient feedback and record the updated symptom score(s) and/or absence or presence of attributes as well as the time at which the feedback was provided. For instance, the patient 106 may indicate that they are feeling nauseous at ten minutes into the treatment session, but then indicate that the nausea has gone away at forty-five minutes into the treatment session, where the computing device 102 would record such events and their corresponding times. In some embodiments, the computing device 102 may provide a sliding scale or other interface element for entering of the updated symptom score. For instance, the computing device 102 may provide a slider with a graphical indication of the symptom score, which, in some cases, may be a face or other graphical indicator that reflects the symptom score. The example illustrated in FIG. 5 and discussed in more detail below illustrates an exemplary graphical indicator, which is a face that dynamically changes based on the symptom score being selected by the patient 106 during the treatment session.

In some cases, the feedback captured from the patient 106 may be manually entered by the patient 106 (e.g., using an input device included in or interfaced with the computing device 102). In some instances, feedback may also be automatically captured by the computing device 102 or another device in communication therewith. For example, the patient 106 may wear a device configured to capture the patient's heart rate and other physiological functions, which may be regularly transmitted to the computing device 102 and captured as part of the feedback for the treatment session.

The computing device 102 may be configured to continue recording patient feedback throughout the treatment session. As part of the recording of patient feedback, the computing device 102 may be configured to alert the patient 106 when a predetermined period of time has passed without the entry of feedback. For instance, the computing device 102 may record a plurality of different feedback entries by the patient 106, but may detect when the patient 106 has not provided feedback for a period of time (e.g., ten minutes) and may alert the patient 106. The alert may be any type of alert that may be performed by the computing device 102, such as an audio tone, visual display, physical movement of the computing device 102 (e.g., vibration), etc. In some cases, the computing device 102 may be configured to enable the patient 106 to select a preferred method of alert. The alert may indicate to the patient 106 that additional feedback is requested, to ensure a proper capturing of data for the treatment session. In some cases, the alert may include a prompt to the patient 106 with respect to one or more of the symptoms being treated, an attribute that is currently presented based on earlier feedback, or an attribute that may be presented based on the medicine 108 (e.g., as discussed below). For instance, the computing device 102 may vibrate and display a prompt asking the patient 106 if they are still nauseous or if their anxiety is still at a score of 8. Such a prompt may further encourage the patient 106 to continually provide beneficial feedback through the treatment session.

In some cases, the predetermined period of time may be based on the medicine 108. For instance, the effects of a medicine 108 or properties thereof (e.g., delivery method, dosage, etc.) may be such that the predetermined period of time may be adjusted due to the frequency of changes experienced by patients 106. For example, edible cannabis may affect patients 106 more slowly over a longer period of time than vaporized cannabis, and thus the predetermined period of time may be longer when the medicine 108 is edible cannabis. Similarly, the computing device 102 may be configured to wait a different period of time before issuing a first alert to the patient 106 when a new treatment session is initiated. For instance, some medicines 108 may have a significant time to take effect, and thus the computing device 102 may not prompt the patient 106 to begin to provide feedback until such a time. For example, if the medicine 108 is edible cannabis, the computing device 102 may not alert the patient 106 to supply feedback until at least forty-five minutes has elapsed since the treatment session began, and may then alert the patient 106 every twenty minutes during instances where feedback has not been provided, whereas, if the medicine 108 is vaporized cannabis, the computing device 102 may issue a first alert at thirty minutes since the start of the treatment session and then every twenty minutes during periods of no feedback being provided. As discussed above, the computing device 102 may only provide alerts in cases where no feedback has been provided for the predetermined period of time since the last feedback. For example, if the patient 106 enters feedback every five to ten minutes on their own, they may never be prompted by the computing device 102 during the treatment session.

In some embodiments, the predetermined periods of time may not be interrupted by automatically captured feedback. For example, if the patient 106 wears a heart rate monitor that automatically provides heart rate data to the computing device 102 during the treatment session, the computing device 102 may still alert the patient 106 for feedback if a predetermined period of time has passed without the patient 106 having manually entered feedback, to ensure updating of data with respect to the symptom(s) being treated and other attributes, in addition to the automatically captured data. In some cases, interruption of the predetermined period of time may be based on the symptom itself. For instance, if the symptom is high blood pressure and is automatically monitored by a device during the treatment session, the patient 106 may not be alerted due to the automatic updating of the treatment of the primary symptom during the session.

The computing device 102 may continue to capture feedback from the patient 106 during the course of the treatment session, and alert the patient 106 as necessary, until the patient 106 instructs the computing device 102 to end the treatment session. In some embodiments, the computing device 102 may be configured to automatically end a treatment session if a specified number of alerts have been issued without the receipt of feedback from the patient 106. In some cases, the computing device 102 may be configured to capture additional feedback from the user at the end of a session, such as a final symptom score for each symptom being treated, and overall rating for the treatment session and/or the medicine, notes provided by the patient 106 regarding the treatment session, etc.

Once the treatment session is completed, the computing device 102 may store the data for the treatment session in a memory thereof. In some embodiments, the computing device 102 may also report the session data to the processing server 104, where the session data may include the data captured for the medicine 108, the symptom scores, presence and absence of attributes, and timestamps related thereto. In cases where the computing device 102 may report to the processing server 104, the reporting data may not include any personally identifiable information without express permission being granted by the patient 106, but may, in some instances, still include information unique to the computing device 102 and/or patient 106 that may be used to aggregate treatment sessions for the patient 106. For example, each patient 106 may be assigned a unique identification number that may be attached to their treatment sessions, but which may not be personally identifiable to the actual patient 106 (e.g., an identification number may be unique to a particular patient while revealing no information about the patient themselves).

In some embodiments, the computing device 102 and/or processing server 104 may be configured to report treatment sessions to a medical professional. For example, the patient 106 may be prescribed the medicine 108 by their physician, who may request that the patient 106 log their consumption of the medicine 108 using the computing device 102. In such an example, the computing device 102 may provide the session data to a suitable computing system, either directly or via the processing server 104. For instance, the computing device 102 may electronically transmit the session data to a health care provider for which the physician works. In these instances, the session data may be accompanied by a unique identifier associated with the patient 106 that may not be personally identifiable to the computing device 102 or processing server 104, but may be used by the medical professional to identify the patient 106 with whom the session is associated. The medical professional may then use the session data in the providing of medical care to the patient 106. In some such embodiments, the computing device 102 may be configured to assist the patient 106 in following a treatment plan set by their medical professional. For instance, the medical professional may set a treatment plan involving consumption of the medicine 108 at specific times and the capturing of feedback related thereto. In such an instance, the computing device 102 may alert the patient 106 when a treatment session is to be conducted as per the professional's treatment plan.

Figure 6:
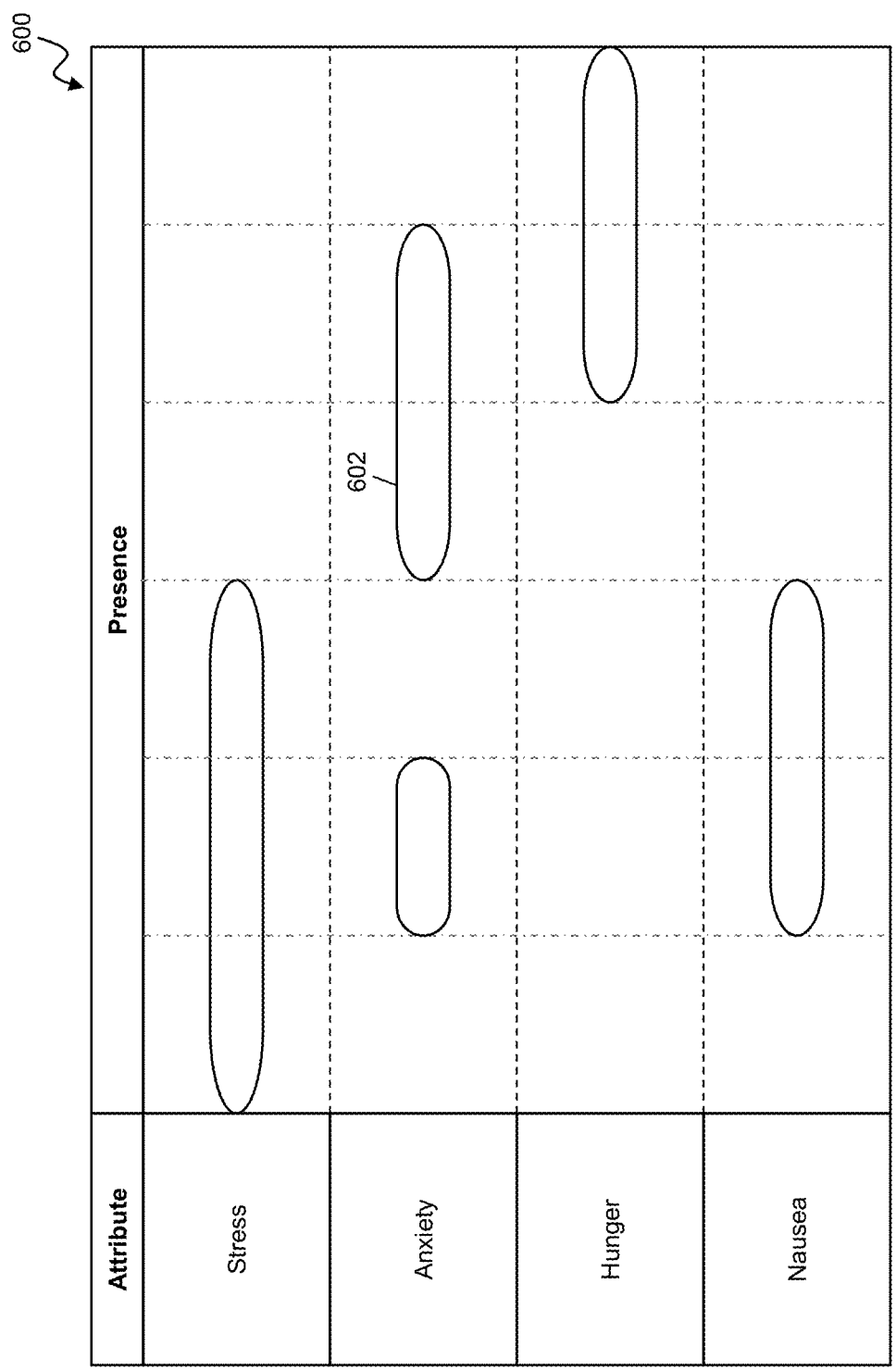
FIG. 6 is a diagram illustrating a graphical user interface for the display of patient feedback captured in real-time as part of a medical treatment in accordance with exemplary embodiments.

In some cases, the computing device 102 may be configured to display a summary or report of a treatment session to the patient 106 once completed. The summary or report may include, for instance, a listing of the feedback provided by the patient 106 at the respective times during the treatment session, the data captured for the medicine 108, the feedback provided by the patient 106 at the end of the session, etc. In some cases, the computing device 102 may be configured to provide a graphical representation of the presence and absence of attributes during the treatment session as indicated in the supplied feedback, such as illustrated in FIG. 6 and discussed in more detail below. In some cases, the computing device 102 may be configured to provide an interface to the patient 106 to compare the treatment session with other sessions, such as sessions using the same batch of medicine 108, other batches of the medicine 108, sessions treating the same symptom(s), etc.

The methods and systems discussed herein may thus accomplish a more accurate capturing of the feedback of a patient 106 for a medical treatment than available using traditional methods. The use of alerts and predetermined periods of time by the computing device 102 can ensure that a sufficient amount of feedback is provided by the patient 106. Furthermore, the capture of such data in real-time may provide for a more comprehensive accounting of the effect of a medicine 108 on the patient 106, which may more greatly increase the quality of care that may be provided to the patient 106.

In some embodiments, the computing device 102 and/or processing server 104 may be configured to identify recommendations for medicines 108 to patients 106 based on captured feedback. In such embodiments, the patient 106 may indicate that they have a symptom that they would like to be treated, such as by entering such an indication into the computing device 102 or communicating the indication to the medicine provider 110 or an employee thereof. The data may then be provided to the processing server 104 or computing device 102, as applicable, which may identify a recommended medicine 108 to treat the patient's symptom. In some embodiments, the recommendation may be based on feedback captured directly from the patient 106. In other embodiments, the recommendation may also be based on feedback captured from other patients 106. For instance, the processing server 104 may receive session data for treatment sessions for a plurality of different patients 106. The processing server 104 may identify the effectiveness of different medicines 108 on different symptoms based on the symptom scores provided by patients 106 during the treatment sessions for the respective medicines 108. When the patient 106 requests treatment of a specific symptom, the processing server 104 may identify a medicine 108 most effective for that symptom across the treatment sessions, and may return that medicine 108 to the computing device 102 or medicine provider 110, as applicable.

In some embodiments, recommendations may also, or alternatively, be based on the physical or chemical properties of medicine 108. For example, if the medicine 108 is cannabis, the physical and/or chemical properties may change greatly from batch to batch, or even from strain to strain. In such cases, the properties may be used to identify a medicine 108 for recommending to the patient 106 for a particular symptom. For example, the patient 106 may use a particular batch of cannabis to treat anxiety, which they find to be really effective for them individually, but may have had less success with other batches of cannabis for the same or different strains. The patient 106 may wish to continue to treat their anxiety once they run out of their particular batch, which may be out of stock or no longer available at the medicine provider 110. The computing device 102 and/or processing server 104 may identify the properties of that particular batch and may identify another batch that mostly closely matches the particular batch in terms of the properties. In some cases, the other batch may be a batch offered by a medicine provider 110 identified by the patient 106. For instance, the patient 106 may request a recommendation among medicines 108 currently available at a specific medicine provider 110 or by any medicine provider 110 within a specific geographic area. As a result, the patient 106 may be able to procure medicine 108 that closely matches a medicine 108 they may have run out of that they have found to be useful for a particular symptom. The use of the physical and/or chemical properties of a particular medicine 108 to identify other medicines 108 may be beneficial for substances that may greatly vary across strains and batches, such as cannabis, and in cases where different patients 106 may react differently to medicines 108. For instance, one patient 106 may find a particular batch of cannabis treats their anxiety very well, while another patient 106 may experience little benefit from the same batch on their own anxiety.

In some embodiments, the processing server 104 and/or computing device 102 may utilize a combination of feedback gathered from a specific patient 106 as well as feedback gathered from other patients 106 for the identification of recommendations for a medicine 108. In such an embodiment, the patient 106 may wish to treat a symptom for which the patient 106 has not yet provided feedback, or has not yet found a medicine 108 that is sufficient at treating that particular symptom. In these embodiments, the processing server 104 (e.g., or computing device 102, as applicable), may identify other patients 106 that have had similar experiences with medicines 108 for which feedback has been captured from the patient 106 seeking the recommendation. For instance, as each patient 106 may react differently to medicines 108, the processing server 104 may identify only those other patients 106 that react similar to the patient 106 seeking the recommendation based on feedback captured therefrom. For example, the patient 106 seeking the recommendation may find a first medicine 108 useful for treating back pain, a second medicine 108 useful for treating nerve pain, and a third medicine 108 useful for treating insomnia. The processing server 104 may identify other patients 106 that have used the same medicines 108 that have also have the same success rate for the associated symptoms to look at their treatment history, rather than look at all patients 106 generally, which may exclude patients 106 that react to medicine 108 differently than the patient 106 seeking the recommendation. The processing server 104 may then identify a medicine 108 to recommend to the patient 106 based on the treatment history for the other patients 106 that were identified as being similar. As a result, the processing server 104 may identify a medicine 108 that is more likely to assist the patient 106 in treating the desired symptom as it had a beneficial effect on other patients 106 that react similar to medication as the patient 106. In cases where the specific medicine 108 may not be available at the preferred medicine provider 110, the processing server 104 may identify an alternative medicine 108 based on the properties thereof, as discussed above. In some embodiments, the computing device 102 and/or processing server 104 may be configured to gather demographic data and other data associated with patients 106 that agree to provide such data, which may be further used to identify similar patients to a patient 106 for the identification of medicine recommendations.

In addition to providing recommendations to patients 106, the processing server 104 may be configured to provide recommendations to medicine providers 110 and medicine manufacturers 112 regarding medicines 108 to carry and produce. For instance, the processing server 104 may receive a significant number of requests from patients 106 in geographic proximity to the medicine provider 110 that are requesting medicines 108 for treating particular symptoms. The processing server 104 may be able to provide this information to the medicine provider 110, to encourage the medicine provider 110 to carry such medicine 108. In some cases, the processing server 104 may be able to recommend specific medicines 108 to carry, such as based on the feedback data captured from treatment sessions as submitted by the patients 106. In some instances, the processing server 104 may recommend specific physical and/or chemical properties related to such symptoms, which may be used by the medicine provider 110 in obtaining medicine 108 to carry.

The processing server 104 may be configured to provide similar data to medicine manufacturers 112. For instance, the processing server 104 may identify physical and/or chemical properties that are associated with treatment of particular symptoms, and may make the information available to medicine manufacturers 112, which may use the properties (e.g., strain information, growth information, storage information, transportation information, etc.) when producing new medicine 108 that may be used to specifically target certain symptoms. For instance, a medicine manufacturer may have a strain that they may grow in a first specific manner that results in stronger effectiveness at treating a specific symptom while also growing a batch of the train in a second specific manner to target a different symptom. Thus, the processing server 104 may be configured to provide useful recommendations to medicine providers 110 and medicine manufacturers 112 in addition to patients 106.

Computing Device

Figure 2:
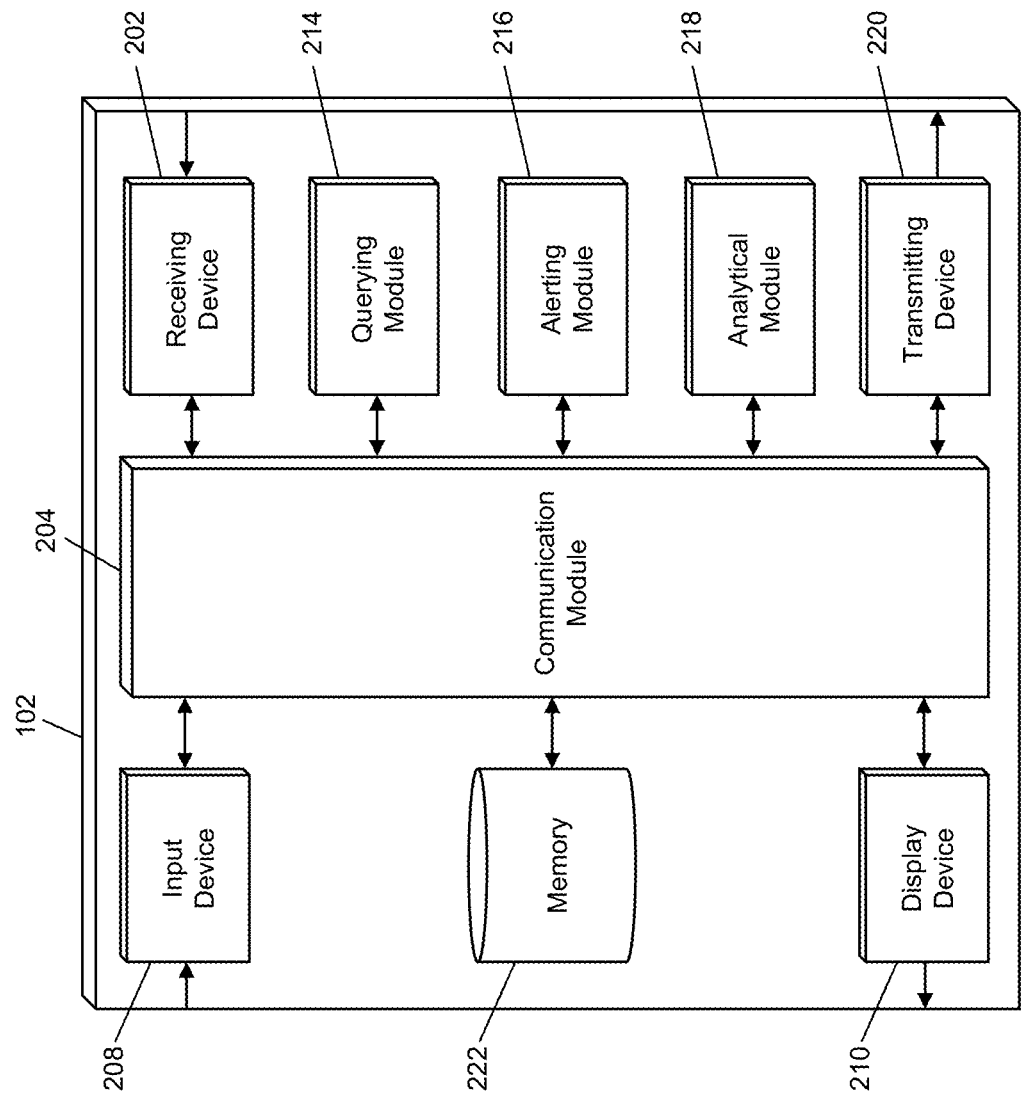
FIG. 2 is a block diagram illustrating the computing device of the system of FIG. 1 for the capturing of patient feedback for a medical treatment and identification of future treatment options in accordance with exemplary embodiments.

FIG. 2 illustrates an embodiment of a computing device 102 in the system 100. It will be apparent to persons having skill in the relevant art that the embodiment of the computing device 102 illustrated in FIG. 2 is provided as illustration only and may not be exhaustive to all possible configurations of the computing device 102 suitable for performing the functions as discussed herein. For example, the computer system 900 illustrated in FIG. 9 and discussed in more detail below may be a suitable configuration of the computing device 102.

The computing device 102 may include a receiving device 202. The receiving device 202 may be configured to receive data over one or more networks via one or more network protocols. In some instances, the receiving device 202 may be configured to receive data from processing servers 104, medicine providers 110, medicine manufacturers 112, and other systems and entities via one or more communication methods, such as radio frequency, local area networks, wireless area networks, cellular communication networks, Bluetooth, the Internet, etc. In some embodiments, the receiving device 202 may be comprised of multiple devices, such as different receiving devices for receiving data over different networks, such as a first receiving device for receiving data over a local area network and a second receiving device for receiving data via the Internet. The receiving device 202 may receive electronically transmitted data signals, where data may be superimposed or otherwise encoded on the data signal and decoded, parsed, read, or otherwise obtained via receipt of the data signal by the receiving device 202. In some instances, the receiving device 202 may include a parsing module for parsing the received data signal to obtain the data superimposed thereon. For example, the receiving device 202 may include a parser program configured to receive and transform the received data signal into usable input for the functions performed by the processing device to carry out the methods and systems described herein.

The receiving device 202 may be configured to receive data signals electronically transmitted by processing servers 104, medicine providers 110, medicine manufacturers 112, or other entities that may be superimposed or otherwise encoded with batch data related to a medicine 108. Batch data may include batch identifiers and/or any properties associated with the medicine 108, such as physical or chemical properties or the particular batch of medicine 108. The receiving device 202 may also be configured to receive data signals electronically transmitted by processing servers 104 that may be superimposed or otherwise encoded with recommendation data, which may recommend one or more medicines 108 and symptoms for treatment thereby. In some cases, the recommendation data may also include data associated with obtaining the medicine(s) 108, such as medicine provider(s) 110 that carry the medicine(s) 108 and geographic locations thereof.

The computing device 102 may also include a communication module 204. The communication module 204 may be configured to transmit data between modules, engines, databases, memories, and other components of the computing device 102 for use in performing the functions discussed herein. The communication module 204 may be comprised of one or more communication types and utilize various communication methods for communications within a computing device. For example, the communication module 204 may be comprised of a bus, contact pin connectors, wires, etc. In some embodiments, the communication module 204 may also be configured to communicate between internal components of the computing device 102 and external components of the computing device 102, such as externally connected databases, display devices, input devices, etc. The computing device 102 may also include a processing device. The processing device may be configured to perform the functions of the computing device 102 discussed herein as will be apparent to persons having skill in the relevant art. In some embodiments, the processing device may include and/or be comprised of a plurality of engines and/or modules specially configured to perform one or more functions of the processing device, such as a querying module 214, alerting module 216, analytical module 218, etc. As used herein, the term "module" may be software or hardware particularly programmed to receive an input, perform one or more processes using the input, and provides an output. The input, output, and processes performed by various modules will be apparent to one skilled in the art based upon the present disclosure.

The computing device 102 may include a memory 222. The memory 222 may be configured to store data for use by the computing device 102 in performing the functions discussed herein, such as public and private keys, symmetric keys, etc. The memory 222 may be configured to store data using suitable data formatting methods and schema and may be any suitable type of memory, such as read-only memory, random access memory, etc. The memory 222 may include, for example, encryption keys and algorithms, communication protocols and standards, data formatting standards and protocols, program code for modules and application programs of the processing device, and other data that may be suitable for use by the computing device 102 in the performance of the functions disclosed herein as will be apparent to persons having skill in the relevant art. In some embodiments, the memory 222 may be comprised of or may otherwise include a relational database that utilizes structured query language for the storage, identification, modifying, updating, accessing, etc. of structured data sets stored therein.

The memory 222 may be configured to store medicine data associated with medicines 108 submitted by the patient 106 or otherwise obtained by the computing device 102 (e.g., from medicine providers 110, etc.). The medicine data may include physical and chemical properties of the related medicine 108, as well as inventory information (e.g., current stock of the medicine 108 by the patient 106), provider information (e.g., where the medicine 108 was obtained, where it is currently carried, etc.), etc. The memory 222 may also be configured to store treatment session data related to treatment sessions captured by the computing device 102 using the methods discussed herein. In some instances, the memory 222 may also be configured to store data related to the treatment of symptoms for the patient 106, such as physical and/or chemical properties found to be effective at treating a symptom, for use in identifying future medicines 108 for treatment of the symptom.

The computing device 102 may also include or be otherwise interfaced with one or more input devices 208. The input devices 208 may be internal to the computing device 102 or external to the computing device 102 and connected thereto via one or more connections (e.g., wired or wireless) for the transmission of data to and/or from. The input devices 208 may be configured to receive input from a user of the computing device 102, which may be provided to another module or engine of the computing device 102 (e.g., via the communication module 204) for processing accordingly. Input devices 208 may include any type of input device suitable for receiving input for the performing of the functions discussed herein, such as a keyboard, mouse, click wheel, scroll wheel, microphone, touch screen, track pad, camera, optical imager, etc. The input device 208 may be configured to, for example, receive input of instructions by the patient 106 related to the beginning and ending of treatment sessions, patient feedback including symptom scores and the presence or absence of attributes, physical or chemical properties of medicine 108, medicine inventory information, etc. The input device 208 may also be configured to read machine-readable codes encoded with batch identifiers and/or properties of medicine 108. In some embodiments, input devices 208 may be configured to automatically capture physiological data of the patient 106 as part of the capturing of patient feedback.

Figure 4:
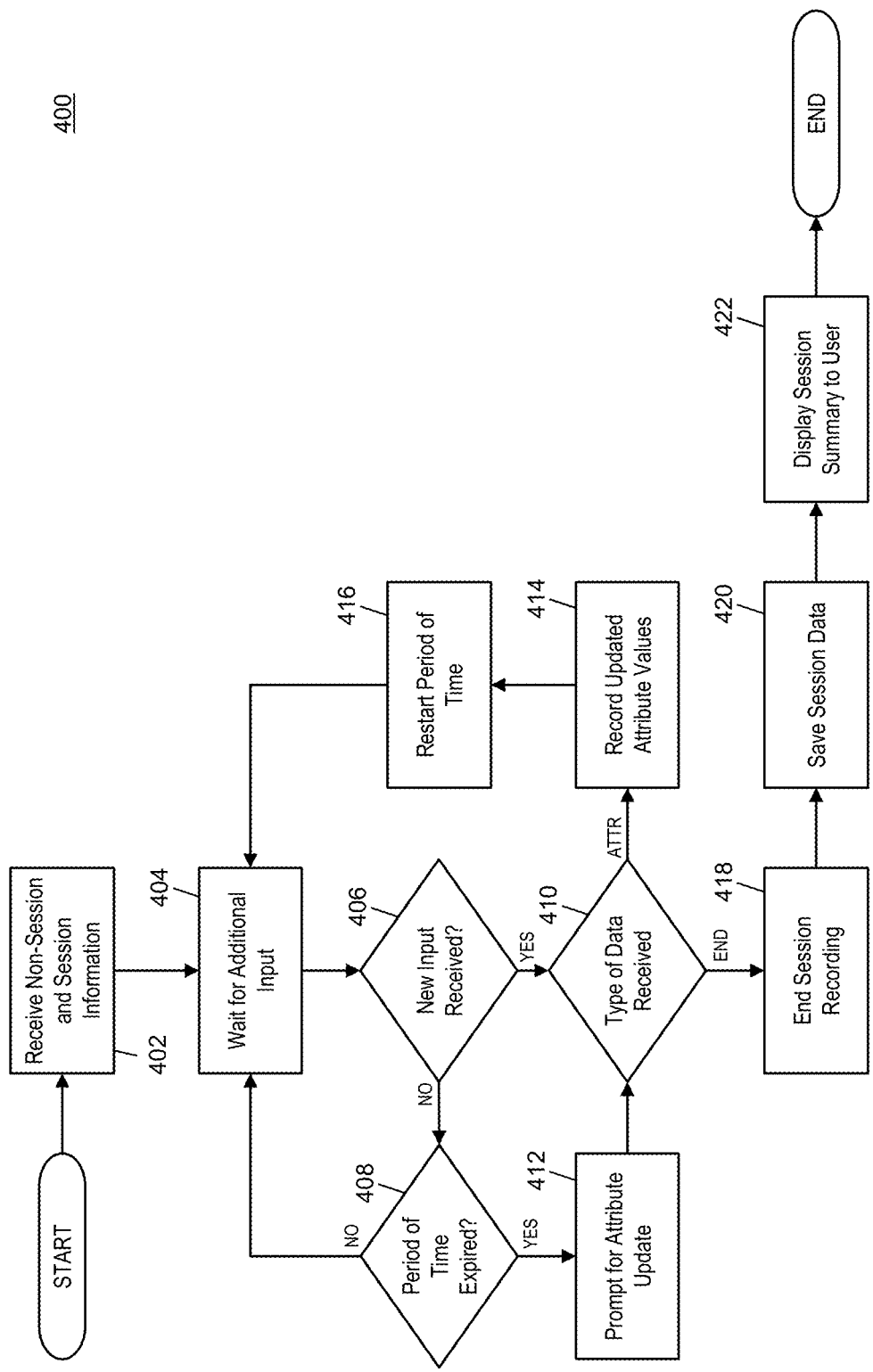
FIG. 4 is a flow diagram illustrating a process for the capturing of patient feedback in real-time for a medical treatment using the computing device of FIG. 2 in accordance with exemplary embodiments.
Figure 5:
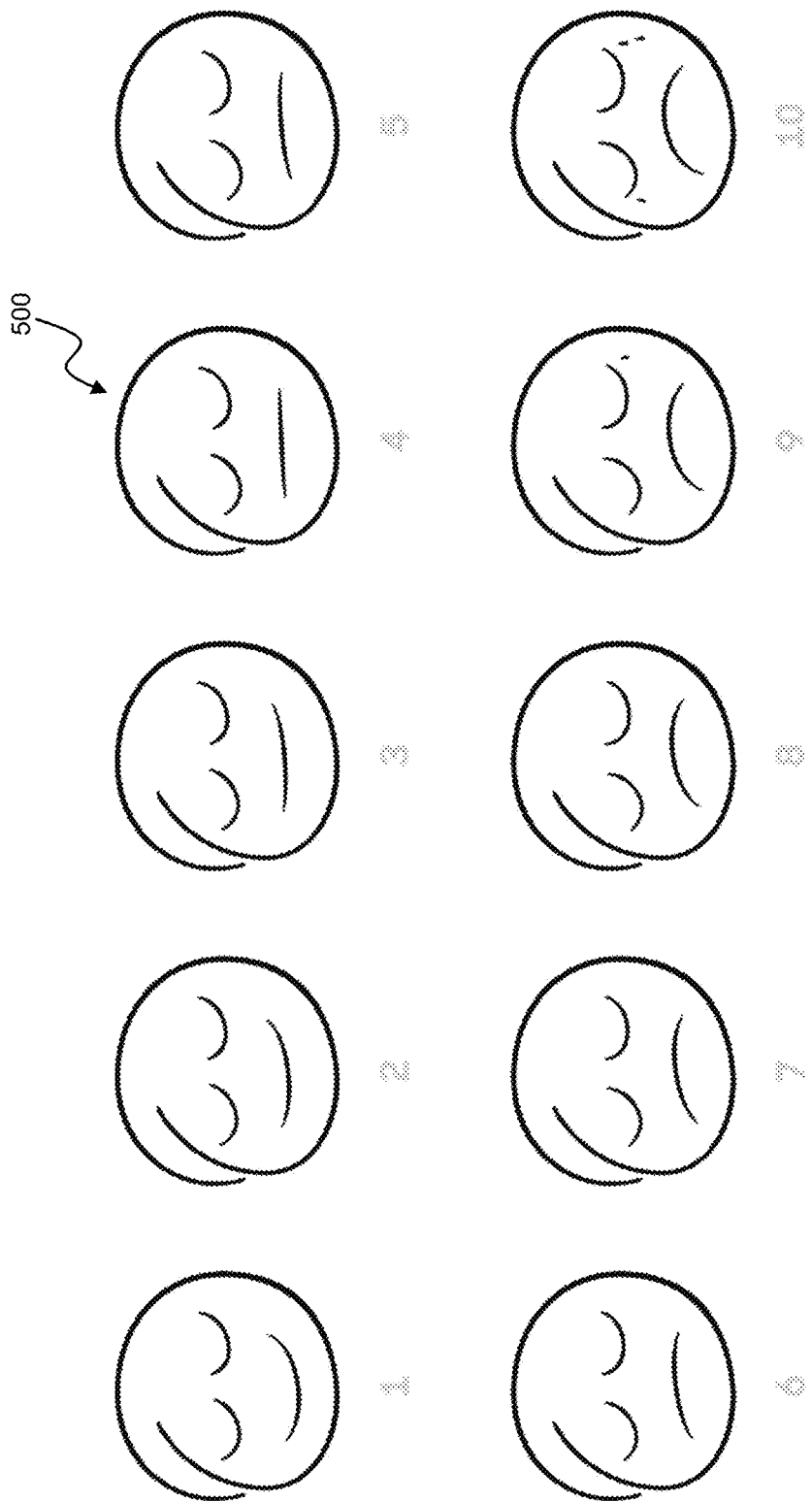
FIG. 5 is a diagram illustrating a graphical user interface element for the representation of a symptom score related to the treatment of a symptom with a given medical treatment in accordance with exemplary embodiments.

The computing device 102 may also include or be otherwise interfaced with a display device 210. The display device 210 may be internal to the computing device 102 or external to the computing device 102 and connected thereto via one or more connections (e.g., wired or wireless) for the transmission of data to and/or from. The display device 210 may be configured to display data to a user of the computing device 102. The display device 210 may be any type of display suitable for displaying data as part of the functions discussed herein, such as a liquid crystal display, light emitting diode display, thin film transistor display, capacitive touch display, cathode ray tube display, light projection display, etc. In some instances, the computing device 102 may include multiple display devices 210. The display device 210 may be configured to, for example, display an interface to the patient 106 as part of the capturing of feedback for treatment sessions, managing of medicines 108, viewing of reports on treatment sessions, the input of and display of data related to recommendations for medicines 108, etc. FIGS. 4 and 5 illustrate example interface elements that may be displayed by the display device 210 as part of the functions discussed herein.

The computing device 102 may include a querying module 214. The querying module 214 may be configured to execute queries on databases to identify information. The querying module 214 may receive one or more data values or query strings, and may execute a query string based thereon on an indicated database, such as the memory 206, to identify information stored therein. The querying module 214 may then output the identified information to an appropriate engine or module of the computing device 102 as necessary. The querying module 214 may, for example, execute a query on the memory 206 to identify treatment session data associated with the patient 106 for use in identifying recommendations of medicine 108 for the treatment of a symptom specified by the patient 106 (e.g., using the input device 208).

The computing device 102 may also include an alerting module 216. The alerting module 216 may be configured to issue alerts to the patient 106 as a user of the computing device 102 for the entry of patient feedback for a treatment session. The alerting module 216 may keep track of times at which patient feedback is entered for a treatment session and, when a predetermined period of time elapses since the last entry of patient feedback, may issue an alert. The alerting module 216 may be configured to issue an alert using any suitable function of the computing device 102, such as a an audio or visual display, controlled movement of the computing device 102 itself, transmission to another device interfaced with the computing device 102 (e.g., a wearable device worn by the patient 106), etc. In some cases, the alerting module 216 may include prompts in the alert, which may be based on currently captured treatment session data (e.g., selected symptoms, present attributes, etc.), to capture feedback from the patient 106. In some instances, the predetermined period of time for alerts, as well as a period of time for issuing of a first alert, may be based on the medicine 108 being consumed and the properties thereof.

The computing device 102 may also include an analytical module 218. The analytical module 218 may be configured to analyze treatment session data, medicine 108 properties, and other data for the identification of recommendations to a patient 106. The analytical module 218 may, for example, analyze session data stored in the memory 222 of the computing device 102 to identify medicine 108 that is effective at treating a specific symptom (e.g., as entered by the patient 106 using the input device 208), and may also analyze the properties of the identified medicine 108 for use in identifying other medicines 108 with the same or similar properties for recommending to the patient 106. The analytical module 218 may also be configured to analyze data associated with treatment sessions and medicines 108 for recommendations related to treatment for the patient 106, such as by recommending specific delivery methods, consumption rates, dosages, times of day to use medicine 108 for a particular symptom, etc., which may be identified based on historical treatment session data captured by the computing device 102.

The computing device 102 may also include a transmitting device 220. The transmitting device 220 may be configured to transmit data over one or more networks via one or more network protocols. In some instances, the transmitting device 220 may be configured to transmit data to processing servers 104, medicine providers 110, medicine manufacturers 112, and other entities via one or more communication methods, local area networks, wireless area networks, cellular communication, Bluetooth, radio frequency, the Internet, etc. In some embodiments, the transmitting device 220 may be comprised of multiple devices, such as different transmitting devices for transmitting data over different networks, such as a first transmitting device for transmitting data over a local area network and a second transmitting device for transmitting data via the Internet. The transmitting device 220 may electronically transmit data signals that have data superimposed that may be parsed by a receiving computing device. In some instances, the transmitting device 220 may include one or more modules for superimposing, encoding, or otherwise formatting data into data signals suitable for transmission.

The transmitting device 220 may be configured to electronically transmit data signals to processing servers 104 that may be superimposed or otherwise encoded with session data related to treatment sessions captured by the computing device 102. In some cases, the session data may include a unique identifier associated with the patient 106 but may not include any personally identifiable information unless expressly authorized by the patient 106. The transmitting device 220 may also be configured to electronically transmit requests for recommendation to processing servers 104, which may include symptoms to be treated, desired physical and/or chemical properties, session data, and any other data that may be used as discussed herein. The transmitting device 220 may also be configured to electronically transmit data signals to medicine providers 110, medicine manufacturers 112, and processing servers 104 that are superimposed or otherwise encoded with a batch identifier, as a request for the properties of a medicine 108 associated therewith.

Processing Server

Figure 3:
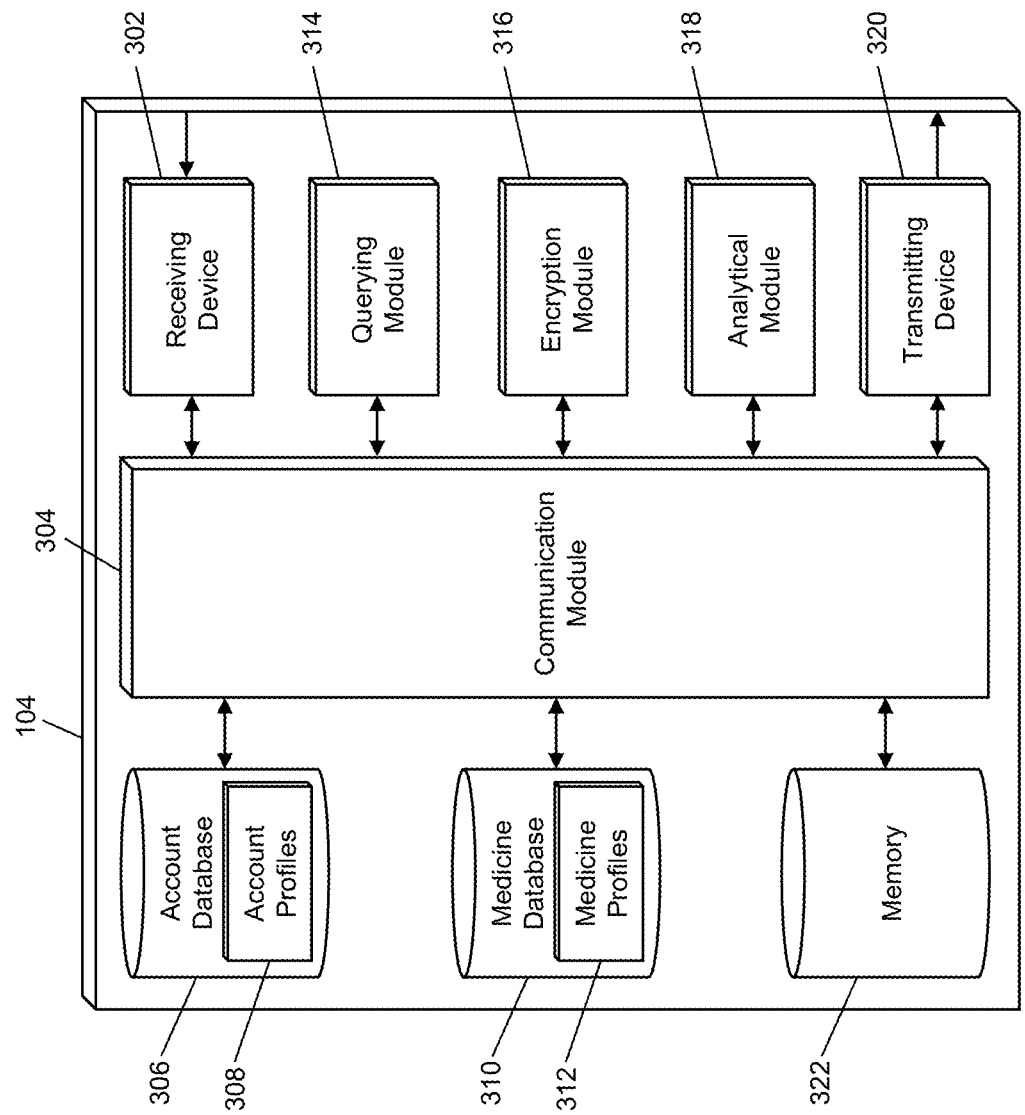
FIG. 3 is a block diagram illustrating the processing server of the system of FIG. 1 for the capturing of patient feedback for a medical treatment and identification of future treatment options in accordance with exemplary embodiments.

FIG. 3 illustrates an embodiment of a processing server 104 in the system 100. It will be apparent to persons having skill in the relevant art that the embodiment of the processing server 104 illustrated in FIG. 3 is provided as illustration only and may not be exhaustive to all possible configurations of the processing server 104 suitable for performing the functions as discussed herein. For example, the computer system 900 illustrated in FIG. 9 and discussed in more detail below may be a suitable configuration of the processing server 104.

The processing server 104 may include a receiving device 302. The receiving device 202 may be configured to receive data over one or more networks via one or more network protocols. In some instances, the receiving device 302 may be configured to receive data from computing devices 102, medicine providers 110, medicine manufacturers 112, and other systems and entities via one or more communication methods, such as radio frequency, local area networks, wireless area networks, cellular communication networks, Bluetooth, the Internet, etc. In some embodiments, the receiving device 302 may be comprised of multiple devices, such as different receiving devices for receiving data over different networks, such as a first receiving device for receiving data over a local area network and a second receiving device for receiving data via the Internet. The receiving device 302 may receive electronically transmitted data signals, where data may be superimposed or otherwise encoded on the data signal and decoded, parsed, read, or otherwise obtained via receipt of the data signal by the receiving device 302. In some instances, the receiving device 302 may include a parsing module for parsing the received data signal to obtain the data superimposed thereon. For example, the receiving device 302 may include a parser program configured to receive and transform the received data signal into usable input for the functions performed by the processing device to carry out the methods and systems described herein.

The receiving device 302 may be configured to receive data signals electronically transmitted by computing devices 102, which may be superimposed or otherwise encoded with treatment session data, requests for recommendations, medicine property data, and other data as discussed herein. The receiving device 302 may also be configured to receive data signals electronically transmitted by medicine providers 110 and medicine manufacturers 112 that are superimposed or otherwise encoded with medicine property data and associated batch identifiers, and/or may be superimposed or otherwise encoded with recommendation requests, which may request recommendations for medicines 108 to carry or manufacture, medicine properties to carry or manufacture, or other data associated therewith.

The processing server 104 may also include a communication module 304. The communication module 304 may be configured to transmit data between modules, engines, databases, memories, and other components of the processing server 104 for use in performing the functions discussed herein. The communication module 304 may be comprised of one or more communication types and utilize various communication methods for communications within a computing device. For example, the communication module 304 may be comprised of a bus, contact pin connectors, wires, etc. In some embodiments, the communication module 304 may also be configured to communicate between internal components of the processing server 104 and external components of the processing server 104, such as externally connected databases, display devices, input devices, etc. The processing server 104 may also include a processing device. The processing device may be configured to perform the functions of the processing server 104 discussed herein as will be apparent to persons having skill in the relevant art. In some embodiments, the processing device may include and/or be comprised of a plurality of engines and/or modules specially configured to perform one or more functions of the processing device, such as a querying module 314, encryption module 316, analytical module 318, etc. As used herein, the term "module" may be software or hardware particularly programmed to receive an input, perform one or more processes using the input, and provides an output. The input, output, and processes performed by various modules will be apparent to one skilled in the art based upon the present disclosure.

The processing server 104 may include an account database 306. The account database 306 may be configured to store a plurality of account profiles 308 using a suitable data storage format and schema. The account database 306 may be a relational database that utilizes structured query language for the storage, identification, modifying, updating, accessing, etc. of structured data sets stored therein. Each account profile 308 may be a structured data set configured to store data related to a patient 106. The account profile 308 may include a unique identifier associated with the patient 106, such as an identification number, but may not include any personally identifiable information unless expressly authorized by the patient 106. The account profile 308 may also include treatment session data captured by a computing device 102 associated with the related patient 106, and any additional data identified from analysis thereof as discussed herein. In instances where a medical professional may request patient treatment data, the account profile 308 related to such a patient 106 may include data for use in providing treatment session data to the medical professional, such as an identification value, medicine 108 for which the session data is requested, communication data for delivering the session data, etc.

The processing server 104 may also include a medicine database 310. The medicine database 310 may be configured to store a plurality of medicine profiles 312 using a suitable data storage format and schema. The medicine database 310 may be a relational database that utilizes structured query language for the storage, identification, modifying, updating, accessing, etc. of structured data sets stored therein. Each medicine profile 312 may be a structured data set configured to store data related to a medicine 108. The medicine profile 312 may include a batch identifier associated with the related medicine 108 or other information useful in identification thereof, property data captured for the medicine 108, and any other data associated therewith that may be identified using the methods and systems discussed herein. For instance, the medicine profile 312 for a medicine 108 may include data related to its effectiveness in treating symptoms based on session data captured by computing devices 102 and provided to the processing server 104. In some cases, a medicine profile 312 may also include data related to medicine manufacturers 112 that manufacture the medicine 108 and medicine providers 110 that carry the medicine 108 for purchase.

The processing server 104 may include a querying module 314. The querying module 314 may be configured to execute queries on databases to identify information. The querying module 314 may receive one or more data values or query strings, and may execute a query string based thereon on an indicated database, such as the account database 306, to identify information stored therein. The querying module 314 may then output the identified information to an appropriate engine or module of the processing server 104 as necessary. The querying module 314 may, for example, execute a query on the account database 306 to insert session data for a new session into an account profile 308 using the unique identifier accompanying the session data, execute a query on the medicine database 310 to identify a medicine profile 312 and property data included therein to provide to a computing device 102, execute queries on the account database 306 to identify account profiles 308 that include session data that may be useful in identification a recommendation, etc.

The processing server 104 may also include an encryption module 316. The encryption module 316 may be configured to encrypt data as part of the functions of the processing server 104 as discussed herein. The encryption module 316 may be configured to encrypt data using one or more encryption techniques using any suitable method of encryption, such as via encryption keys, hashes, salts, ciphers, etc. The encryption module 316 may be configured to encrypt data that is electronically transmitted from the processing server 104 or that is stored therein to increase the security of such data. For instance, any data provided to medical professionals may be encrypted prior to transmission to protect patient privacy.

The processing server 104 may also include an analytical module 318. The analytical module 318 may be configured to analyze treatment session data, medicine 108 properties, and other data for the identification of recommendations to patients 106, medicine providers 110, medicine manufacturers 112, etc. The analytical module 318 may, for example, analyze session data stored in account profiles 308 of the account database 306 to identify medicine 108 that is effective at treating a specific symptom (e.g., as requested by a patient 106, medicine provider 110, etc.), and may also analyze the properties of the identified medicine 108 for use in identifying other medicines 108 with the same or similar properties for recommending to patients 106. The analytical module 318 may also be configured to analyze data associated with treatment sessions and medicines 108 for recommendations related to treatment for patients 106, such as by recommending specific delivery methods, consumption rates, dosages, times of day to use medicine 108 for a particular symptom, etc., which may be identified based on historical treatment session data stored in the account profile 308 associated with the specific patient 106.

The processing server 104 may also include a transmitting device 320. The transmitting device 320 may be configured to transmit data over one or more networks via one or more network protocols. In some instances, the transmitting device 320 may be configured to transmit data to computing devices 102, medicine providers 110, medicine manufacturers 112, and other entities via one or more communication methods, local area networks, wireless area networks, cellular communication, Bluetooth, radio frequency, the Internet, etc. In some embodiments, the transmitting device 320 may be comprised of multiple devices, such as different transmitting devices for transmitting data over different networks, such as a first transmitting device for transmitting data over a local area network and a second transmitting device for transmitting data via the Internet. The transmitting device 320 may electronically transmit data signals that have data superimposed that may be parsed by a receiving computing device. In some instances, the transmitting device 320 may include one or more modules for superimposing, encoding, or otherwise formatting data into data signals suitable for transmission.

The transmitting device 320 may be configured to electronically transmit data signals to computing devices 102, medicine providers 110, medicine manufacturers 112, or other entities that may be superimposed or otherwise encoded with recommendations related to the treatment of symptoms, which may include medicine 108 recommendations, medicine properties, treatment methods, etc. The transmitting device 320 may also be configured to electronically transmit data signals to third party entities related to medical professionals that are superimposed or otherwise encoded with session data, such as in cases where a patient 106 is to report their treatment sessions to a health care professional. In such embodiments, such data may be encrypted (e.g., via the encryption module 316) prior to transmission.

The processing server 104 may include a memory 322. The memory 322 may be configured to store data for use by the processing server 104 in performing the functions discussed herein, such as public and private keys, symmetric keys, etc. The memory 322 may be configured to store data using suitable data formatting methods and schema and may be any suitable type of memory, such as read-only memory, random access memory, etc. The memory 322 may include, for example, encryption keys and algorithms, communication protocols and standards, data formatting standards and protocols, program code for modules and application programs of the processing device, and other data that may be suitable for use by the processing server 104 in the performance of the functions disclosed herein as will be apparent to persons having skill in the relevant art. In some embodiments, the memory 322 may be comprised of or may otherwise include a relational database that utilizes structured query language for the storage, identification, modifying, updating, accessing, etc. of structured data sets stored therein.

Process for Capturing of Patient Feedback for a Treatment Session

FIG. 4 illustrates a process 400 for the capturing of patient feedback in real-time during a treatment session for a medical treatment using the computing device 102 of the system 100.

In step 402, the input device 208 of the computing device 102 may receive session information as input by the patient 106 and any other sources, which may include at least information identifying the medicine 108 being consumed, one or more symptoms being treated, the method of ingestion, and an initial symptom score for each symptom. In some cases, step 402 may include the receipt of property data for the medicine 108, such as from the medicine provider 110, by the reading and decoding of a machine-readable code displayed on the medicine 108, etc. Step 402 may also include the receipt of non-session information, which may be used by the computing device 102 or provided with the session results, which may include any data not specific to the treatment session, such as patient data (e.g., age, weight, demographics, etc.), historical treatment data, inventory data, etc. In step 404, the treatment session may continue with the input device 208 awaiting the entry of any new input from the patient 106 as part of the treatment session.

In step 406, the computing device 102 may determine if any new inputs have been received from the patient 106 via the input device 208. If no inputs have been received (e.g., the treatment session has continued without new feedback submitted by the patient 106), then, in step 408, the computing device 102 may determine if the predetermined period of time for supplying feedback has expired. In some instances, the predetermined period of time may be based on the medicine 108 being used in the treatment session. If the predetermined period of time has not yet expired, then the process 400 may return to step 404 and continue to wait for additional inputs to be received as the treatment session progresses.

If, in step 408, the computing device 102 determines that the predetermined period of time has expired, then, in step 412, the alerting module 216 of the computing device 102 may issue an alert to the patient 106 that includes a prompt (e.g., displayed via the display device 210 of the computing device 102) prompting the patient 106 to update the attributes (e.g., including the symptom score(s)) for their treatment session. The patient 106 may be prompted and then supply (e.g., via the input device 208) feedback.

In step 410, the computing device 102 may identify the type of feedback that is provided by the patient 106, such as in response to a prompt displayed in step 412 or input received as determined in step 406. The type of feedback may be identified based on the instructions as submitted therewith and/or data included in the feedback. In one instance, the feedback may include attribute information, which may include an updated symptom score for one or more of the symptoms being treated, notes written or documented by the patient 106, and/or the presence or absence of one or more attributes experienced during the treatment session. If such feedback is received, then, in step 414, the querying module 214 of the computing device 102 may execute a query on the memory 222 therein to store the received attribute values along with the time at which they were submitted as part of the session data for the treatment session. In step 416, the alerting module 216 may restart the predetermined period of time, such that the patient 106 will not be alerted if they continue to provide regular feedback.

In another instance, the feedback may be an instruction indicating that the treatment session should be ended. If such feedback is received, then, in step 418, the recording of the treatment session may be ended by the computing device 102. In some embodiments, the ending of the treatment session may include prompting the patient 106 to supply end of session data, which may include a rating of the session and/or medicine 108, a final symptom score, an accounting of any present attributes, the supplying of personal notes regarding the session, additional survey questions, etc. In step 420, the querying module 214 may execute a query on the memory 222 of the computing device 102 to store the session data therein. In some embodiments, step 420 may include the electronic transmission of the session data to the processing server 104 by the transmitting device 220 of the computing device 102, where the session data may be accompanied by a unique identifier associated with the patient 106. In step 422, the display device 210 may display session data to the patient 106, which may, in some instances, be analyzed (e.g., via the analytical module 218 of the computing device 102) prior to display or otherwise modified or processed, such as a report developed based thereon for presentation to the patient 106. For instance, the session data may be compared with other session data to provide results to the patient 106 regarding what medicine properties have what effects on their symptoms or other attributes, effectiveness of delivery methods and dosages, etc.

Graphical User Interfaces

FIGS. 5 and 6 illustrate example graphical user interface elements of the computing device 102, such as may be displayed to the patient 106 via the display device 210 thereof as part of the capturing and presentation of patient feedback for treatment sessions, such as a treatment session captured using the process 400 illustrated in FIG. 4 and discussed above.

FIG. 5 illustrates ten different iterations of a graphical illustration 500. The graphical illustration 500 illustrated in FIG. 5 may be a graphical representation of the effect of a symptom on the patient 106 based on their supplied symptom score. For instance, the display device 210 of the computing device 102 may display a slider or some other input method that may be used by the patient 106 so submit a symptom score, where the graphical illustration 500 corresponding to the entered symptom score may be displayed. For instance, a symptom score of 10 may display the corresponding graphical illustration as illustrated in FIG. 5. As the patient 106 adjusts their symptom score, the graphical illustration 500 may dynamically change, such as via an animation to seamlessly change from one graphical illustration to the next. In some cases, the graphical illustration 500 may be displayed throughout the treatment session, where the patient 106 may be able to adjust and update their symptom score throughout the treatment session.

FIG. 6 illustrates a chart 600 that may be presented to the patient 106 during their treatment session or after a treatment session (e.g., as part of the reporting of the treatment session or at a later time when viewing the results of a treatment session). The chart 600 illustrates the presence 602 of attributes throughout a treatment session, such as indicated by the patient 106 during feedback captured by the computing device 102. In the illustrated example, the patient 106 may take a medicine 108 during the treatment session where they are experiencing stress from the start of the treatment session, which goes away halfway through, and may experience intermittent anxiety and a brief period of nausea that is followed by hunger after the nausea dissipates. The chart 600 may be used by the patient 106 as a graphical representation of their treatment session, which may be used by the patient 106 in future treatment decisions. For instance, the patient 106 may find the particular medicine 108 useful for reducing stress, but may want to also take additional medicine 108 that is useful against anxiety so reduce such effects by the particular medicine 108.

Identifying Medicine Recommendations Based on Patient Feedback

Figure 7:
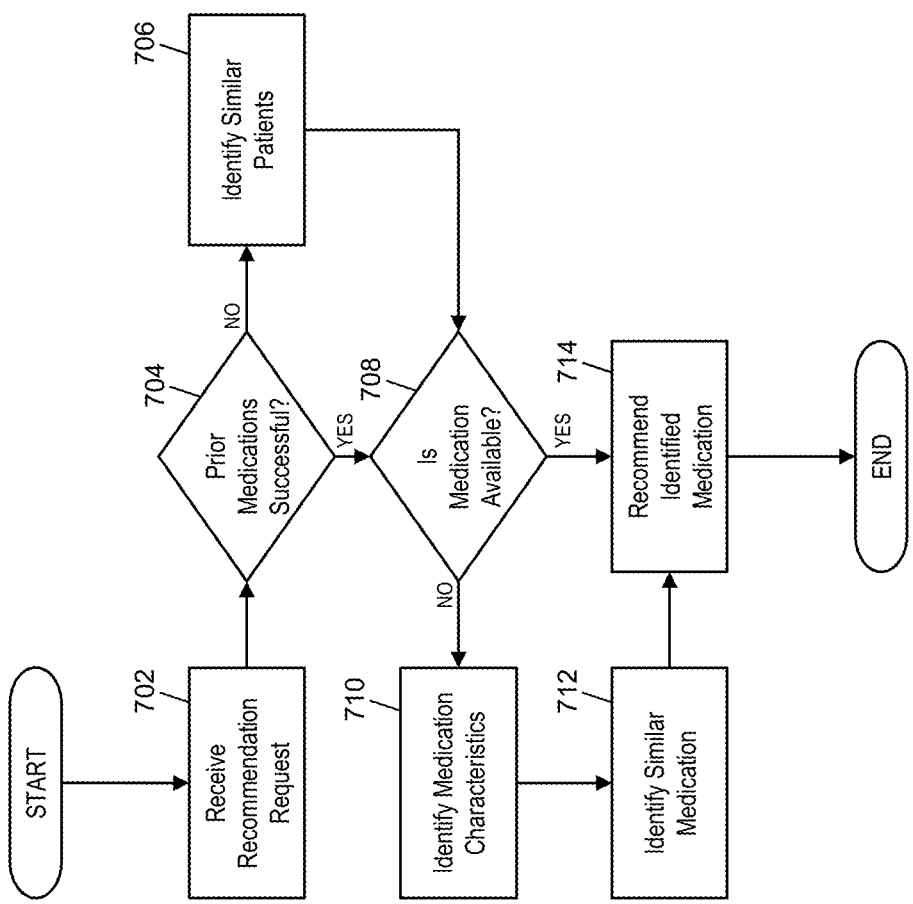
FIG. 7 is a flow diagram illustrating a process for the identification of a recommended treatment option for one or more symptoms based on captured patient feedback using the system of FIG. 1 in accordance with exemplary embodiments.

FIG. 7 illustrates a process 700 for the identification of medicine 108 for recommending to a patient 106 in the system 100 based on patient feedback submitted by the patient 106 and other patients 106 for the treatment of one or more symptoms. It will be apparent to persons having skill in the relevant art that, while the process 700 is described as being executed by the processing server 104 and the components thereof, the process 700 may also, or alternatively, be executed by the computing device 102 using the components thereof as discussed herein.

In step 702, the receiving device 302 of the processing server 104 may receive a request for a recommendation from the patient 106 via a computing device 102 associated therewith. The request for a recommendation may include at least one symptom that the patient 106 desires to be treated, as well as a unique identifier associated with the patient 106. In some embodiments, the request may also include session data associated with treatment sessions captured by the computing device 102 for the patient 106. In other embodiments, the querying module 314 of the processing server 104 may, upon receipt of the request, execute a query on the account database 306 of the processing server 104 to identify an account profile 308 associated with the patient 106 as identified using the unique identifier, for identification of the session data included therein.

In step 704, the analytical module 318 of the processing server 104 may analyze the session data for the patient 106 to determine if any prior medicines 108 used by the patient 106 have been successful in treating the identified symptom(s). The determination may be based on symptom scores provided by the patient 106 during the treatment sessions where a given medicine 108 was taken, where success may be identified via treatment sessions where a significant change in symptom score occurred, and may also be based on other feedback (e.g., session/medicine ratings) provided by the patient 106. If no prior medicines 108 have been taken by the patient 106 that were sufficiently successful for the identified symptom(s), then, in step 706, the analytical module 318 of the processing server 104 may identify one or more other patients that are similar to the patient 106 to identify a suitable medicine 108. Similar patients may be identified based on session data (e.g., stored in corresponding account profiles 308) where the patient experiences the same or similar effects on symptom scores and attributes, or provides similar ratings, when taken medicines 108 as had been taken by the patient 108. The analytical module 318 may identify such patients and may then identify if the similar patients had taken any medicine 108 that was effective for the symptom(s) identified by the patient 106.

Once a suitable medicine 108 has been identified, either based on the patient's own session data in step 704 or the session data of similar patients in step 706, then, in step 708, the processing server 104 may identify if that medicine 108 is available to the patient 106. The availability may be determined based on, for instance, current stock of a preferred medicine provider 110 for the patient 106 (e.g., as indicated in their request or their corresponding account profile 308) or of medicine providers 110 in a geographic area identified by the patient 106. If the medicine 108 is available, then, in step 714, the transmitting device 320 of the processing server 104 may electronically transmit information associated with the medicine 108 to the computing device 102 for display to the patient 106. Such information may include, for instance, the name of the medicine 108, recommended delivery methods and dosages, locations of medicine providers 110 where the medicine 108 may be obtained, etc.

If the medicine 108 is not available, then, in step 710, the processing server 104 may identify the characteristics of the medicine 108, which may include the physical and chemical properties of the medicine 108. In one embodiment, the characteristics may be identified via the querying (e.g., by the querying module 314) of the medicine database 310 of the processing server 104 to identify a medicine profile 312 associated with the medicine 108 where the characteristics may be stored therein. In another embodiment, the transmitting device 320 of the processing server 104 may electronically transmit a characteristic request to a third party, such as a medicine provider 110 or medicine manufacturer 112, requesting the characteristics for the identified medicine 108, and may receive the characteristics therefrom via the receiving device 302.

Once the characteristics are identified, then, in step 712, the processing server 104 may identify a similar medicine 108. The similar medicine 108 may be another medicine that has medication characteristics that are the same or similar to the identified medicine 108 based on its own characteristics (e.g., identified similarly, as in step 710). In some cases, the similar medicine 108 may be another medicine 108 that was identified to be effective in steps 704 and/or 706 that may be obtained at the medicine provider 110. In some embodiments, a similar medicine 108 may only be identified if it is available at an eligible medicine provider 110. Once the similar medicine 108 is identified, the process 700 may proceed to step 714 where the recommendation for the similar medicine 108 is transmitted to the patient 106 via the computing device 102. The patient 106 may then obtain the medicine 108 to treat their desired symptom.

Exemplary Method for Capturing Patient Feedback for a Medical Treatment

Figure 8:
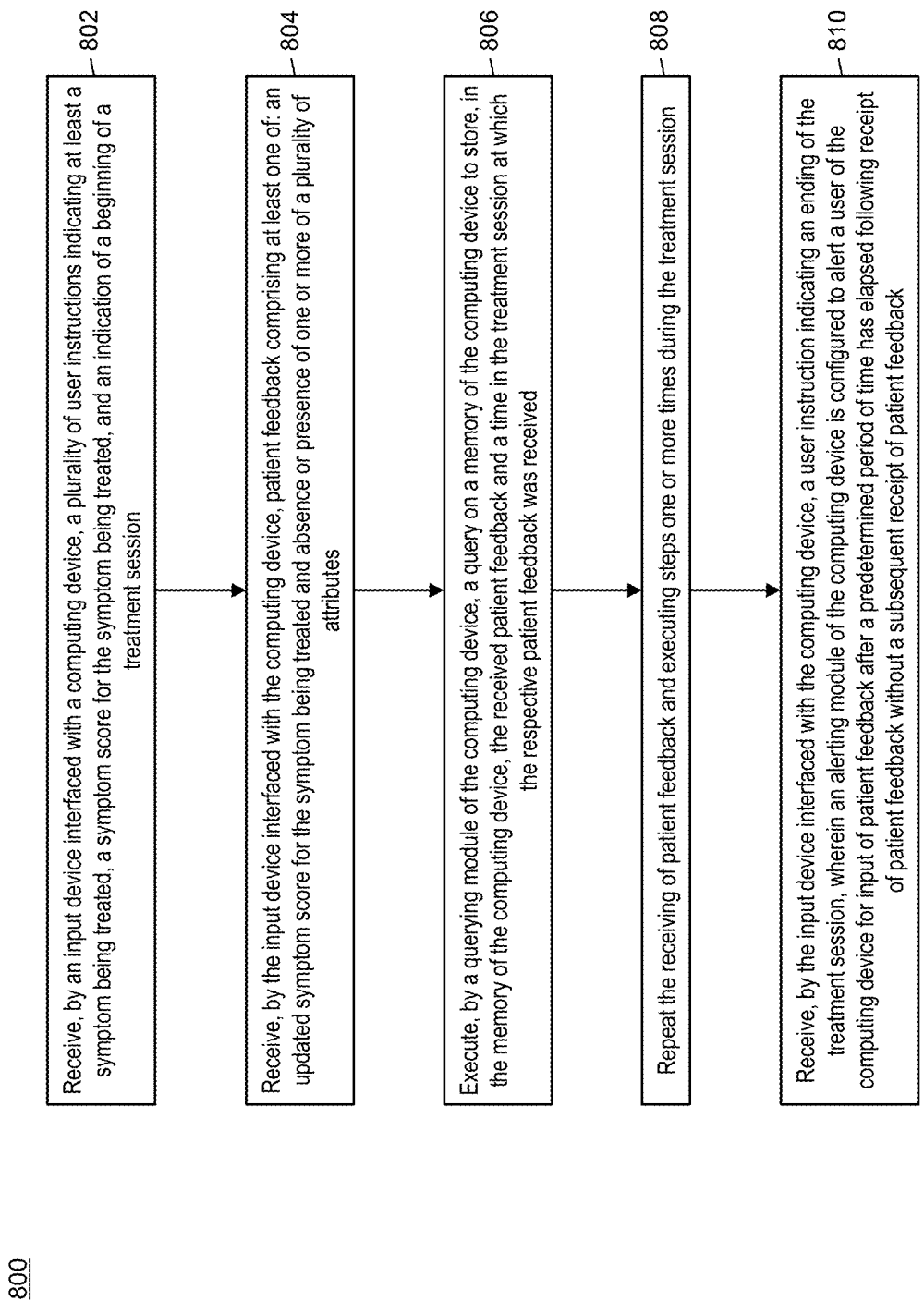
FIG. 8 is a flow chart illustrating an exemplary method for the capturing of patient feedback for a medical treatment in accordance with exemplary embodiments.

FIG. 8 illustrates a method 800 for the capturing of patient feedback in real-time for a medical treatment including the score of a symptom being experienced and the presence and/or absence of one or more attributes.

In step 802, a plurality of user instructions may be received by an input device (e.g., an input device 208) interfaced with a computing device (e.g., the computing device 102), wherein the user instructions indicate at least a symptom being treated, a symptom score for the symptom being treated, and an indication of a beginning of a treatment session. In step 804, patient feedback may be received by the input device of the computing device, wherein the patient feedback comprises at least one of: an updated symptom score for the symptom being treated and absence or presence of one or more of a plurality of attributes.

In step 806, a query may be executed on a memory (e.g., the memory 222) of the computing device by a querying module (e.g., the querying module 314) to store, in the memory of the computing device, the received patient feedback and a time in the treatment session at which the respective patient feedback was received. In step 808, the receiving of patient feedback and executing steps may be repeated one or more times during the treatment session. In step 810, a user instruction may be received by the input device interfaced with the computing device that indicates an ending of the treatment session. As part of the method 800, an alerting module (e.g., the alerting module 216) of the computing device 102 may be configured to alert a user (e.g., the patient 106) of the computing device for input of patient feedback after a predetermined period of time has elapsed following receipt of patient feedback without a subsequent receipt of patient feedback.

In one embodiment, the plurality of user instructions may further include a medication delivery method, and the predetermined period of time may be based on the medication delivery method. In some embodiments, the alert may be delivered using at least one of: an audio emitting device interfaced with the computing device configured to emit an audio signal and a display device (e.g., the display device 210) interfaced with the computing device configured to display a notification message.

In one embodiment, the method 800 may further include displaying, by a display device interfaced with the computing device, a scale associated with the symptom score for use by the user of the computing device to input patient feedback including updated symptom scores. In a further embodiment, the scale may incorporate a slider and may be accompanied by a graphical display configured to update based on the updated symptom score corresponding to a position of the slider.

In some embodiments, the method 800 may also include displaying, by a display device interfaced with the computing device, a summary of the treatment session after the ending of the treatment session, wherein the summary includes a visual indication of the absence and presence of the plurality of attributes during the treatment session based on the respective patient feedback. In a further embodiment, the visual indication may be displayed along a time scale spanning the treatment session and displays only attributes for which patient feedback was received. In one embodiment, the plurality of user instructions may further include at least one of: medication type, medication amount, dosage amount, concentration, strain, batch, delivery method, administration time, and chemical data.

Computer System Architecture

Figure 9:
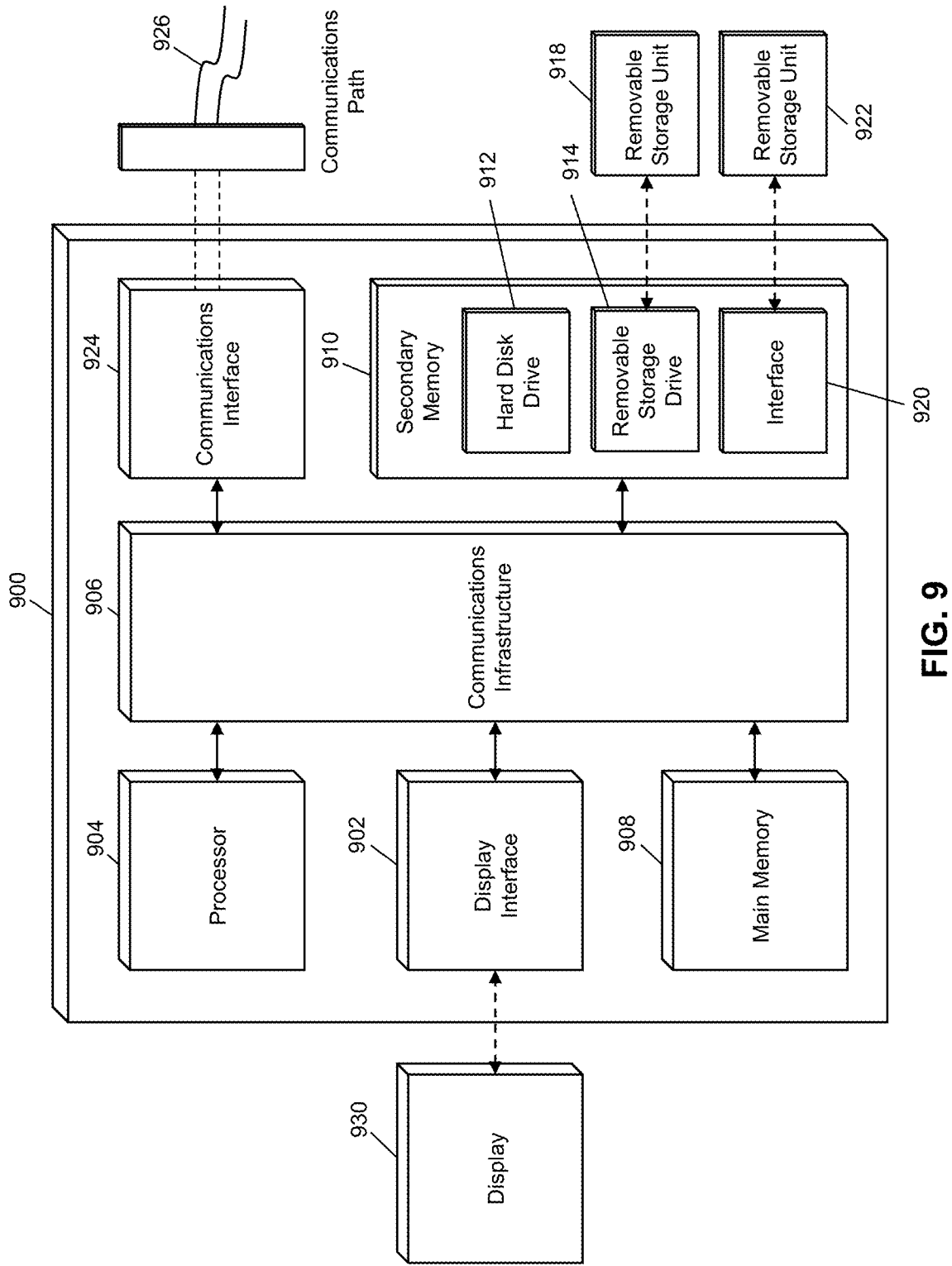
FIG. 9 is a block diagram illustrating a computer system architecture in accordance with exemplary embodiments.

FIG. 9 illustrates a computer system 900 in which embodiments of the present disclosure, or portions thereof, may be implemented as computer-readable code. For example, the computing device 102 and processing server 104 of FIG. 1 may be implemented in the computer system 900 using hardware and non-transitory computer readable media having specifically configured instructions stored thereon, and may be implemented in one or more computer systems or other processing systems. Hardware, software, or any combination thereof may embody modules and components used to implement the methods of FIGS. 4, 7, and 8.

If programmable logic is used, such logic may execute on a commercially available processing platform that has been specially configured to become a specific purpose computer or a special purpose device (e.g., programmable logic array, application-specific integrated circuit, etc.) configured to perform the functions discussed herein. A person having an ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device, provided they are specifically configured to perform the disclosed functions. For instance, at least one processor device and a memory may be used to implement the above described embodiments.

A processor unit or device as discussed herein may be a single processor, a plurality of processors, or combinations thereof. Processor devices may have one or more processor "cores." The terms "computer program medium," "non-transitory computer readable medium," and "computer usable medium" as discussed herein are used to generally refer to tangible media such as a removable storage unit 918, a removable storage unit 922, and a hard disk installed in hard disk drive 912.

Various embodiments of the present disclosure are described in terms of this example computer system 900. After reading this description, it will become apparent to a person skilled in the relevant art how to implement the present disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 904 may be a special purpose or a general purpose processor device specifically configured to perform the functions discussed herein. The processor device 904 may be connected to a communications infrastructure 906, such as a bus, message queue, network, multi-core message-passing scheme, etc. The network may be any network suitable for performing the functions as disclosed herein and may include a local area network (LAN), a wide area network (WAN), a wireless network (e.g., WiFi), a mobile communication network, a satellite network, the Internet, fiber optic, coaxial cable, infrared, radio frequency (RF), or any combination thereof. Other suitable network types and configurations will be apparent to persons having skill in the relevant art. The computer system 900 may also include a main memory 908 (e.g., random access memory, read-only memory, etc.), and may also include a secondary memory 910. The secondary memory 910 may include the hard disk drive 912 and a removable storage drive 914, such as a floppy disk drive, a magnetic tape drive, an optical disk drive, a flash memory, etc.

The removable storage drive 914 may read from and/or write to the removable storage unit 918 in a well-known manner. The removable storage unit 918 may include a removable storage media that may be read by and written to by the removable storage drive 914. For example, if the removable storage drive 914 is a floppy disk drive or universal serial bus port, the removable storage unit 918 may be a floppy disk or portable flash drive, respectively. In one embodiment, the removable storage unit 918 may be non-transitory computer readable recording media.

In some embodiments, the secondary memory 910 may include alternative means for allowing computer programs or other instructions to be loaded into the computer system 900, for example, the removable storage unit 922 and an interface 920. Examples of such means may include a program cartridge and cartridge interface (e.g., as found in video game systems), a removable memory chip (e.g., EEPROM, PROM, etc.) and associated socket, and other removable storage units 922 and interfaces 920 as will be apparent to persons having skill in the relevant art.

Data stored in the computer system 900 (e.g., in the main memory 908 and/or the secondary memory 910) may be stored on any type of suitable computer readable media, such as optical storage (e.g., a compact disc, digital versatile disc, Blu-ray disc, etc.) or magnetic tape storage (e.g., a hard disk drive). The data may be configured in any type of suitable database configuration, such as a relational database, a structured query language (SQL) database, a distributed database, an object database, etc. Suitable configurations and storage types will be apparent to persons having skill in the relevant art.

The computer system 900 may also include a communications interface 924. The communications interface 924 may be configured to allow software and data to be transferred between the computer system 900 and external devices. Exemplary communications interfaces 924 may include a modem, a network interface (e.g., an Ethernet card), a communications port, a PCMCIA slot and card, etc. Software and data transferred via the communications interface 924 may be in the form of signals, which may be electronic, electromagnetic, optical, or other signals as will be apparent to persons having skill in the relevant art. The signals may travel via a communications path 926, which may be configured to carry the signals and may be implemented using wire, cable, fiber optics, a phone line, a cellular phone link, a radio frequency link, etc.

The computer system 900 may further include a display interface 902. The display interface 902 may be configured to allow data to be transferred between the computer system 900 and external display 930. Exemplary display interfaces 902 may include high-definition multimedia interface (HDMI), digital visual interface (DVI), video graphics array (VGA), etc. The display 930 may be any suitable type of display for displaying data transmitted via the display interface 902 of the computer system 900, including a cathode ray tube (CRT) display, liquid crystal display (LCD), light-emitting diode (LED) display, capacitive touch display, thin-film transistor (TFT) display, etc.

Computer program medium and computer usable medium may refer to memories, such as the main memory 908 and secondary memory 910, which may be memory semiconductors (e.g., DRAMs, etc.). These computer program products may be means for providing software to the computer system 900. Computer programs (e.g., computer control logic) may be stored in the main memory 908 and/or the secondary memory 910. Computer programs may also be received via the communications interface 924. Such computer programs, when executed, may enable computer system 900 to implement the present methods as discussed herein. In particular, the computer programs, when executed, may enable processor device 904 to implement the methods illustrated by FIGS. 4, 7, and 8, as discussed herein. Accordingly, such computer programs may represent controllers of the computer system 900. Where the present disclosure is implemented using software, the software may be stored in a computer program product and loaded into the computer system 900 using the removable storage drive 914, interface 920, and hard disk drive 912, or communications interface 924.

The processor device 904 may comprise one or more modules or engines configured to perform the functions of the computer system 900. Each of the modules or engines may be implemented using hardware and, in some instances, may also utilize software, such as corresponding to program code and/or programs stored in the main memory 908 or secondary memory 910. In such instances, program code may be compiled by the processor device 904 (e.g., by a compiling module or engine) prior to execution by the hardware of the computer system 900. For example, the program code may be source code written in a programming language that is translated into a lower level language, such as assembly language or machine code, for execution by the processor device 904 and/or any additional hardware components of the computer system 900. The process of compiling may include the use of lexical analysis, preprocessing, parsing, semantic analysis, syntax-directed translation, code generation, code optimization, and any other techniques that may be suitable for translation of program code into a lower level language suitable for controlling the computer system 900 to perform the functions disclosed herein. It will be apparent to persons having skill in the relevant art that such processes result in the computer system 900 being a specially configured computer system 900 uniquely programmed to perform the functions discussed above.

Techniques consistent with the present disclosure provide, among other features, systems and methods for capturing patient feedback for a medical treatment. While various exemplary embodiments of the disclosed system and method have been described above it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope.

What is claimed is:

1. A method for capturing user feedback, comprising:
receiving, by an input device interfaced with a computing processor, a plurality of user instructions indicating (i) a symptom, condition or ailment, (ii) a score associated with at least one of the symptom, condition or ailment, and (iii) an indication of a session for addressing at least one of the symptom, condition or ailment;
receiving, by the input device interfaced with the computing processor, user feedback comprising at least one of: an updated score and absence or presence of attributes;
executing, by a querying module of the computing processor, a query on at least one of a memory internal to the computing processor and external to the computing processor to store, the received user feedback;
repeating the receiving of user feedback and executing steps;
alerting, by the computing processor, the user for input of user feedback after a predetermined period of time has elapsed following receipt of the user feedback without a subsequent receipt of user feedback; and
displaying, by a display interfaced with the computing processor, a scale associated with the score for use by the user of the computing processor to input user feedback including updated scores, wherein the scale incorporates a graphic user interface and is accompanied by a graphical display configured to update based on the updated score corresponding to a value of the graphic user interface.

2. The method of claim 1, further comprising:
receiving, by the input device interfaced with the computing processor, a user instruction indicating an ending of the session.

3. The method of claim 1, wherein
the plurality of user instructions further includes a product delivery method, and
the predetermined period of time is based on the product delivery method.

4. The method of claim 1, wherein the alert is delivered using at least one of: an audio emitting device configured to emit an audio signal and a display configured to display a message.

5. The method of claim 1, further comprising:
displaying, by a display interfaced with the computing processor, a summary of the session after the ending of the session, wherein the summary includes a visual and/or written indication of the absence and presence of the plurality of attributes during the session based on the respective user feedback.

6. The method of claim 5, wherein the visual and/or written indication is displayed and only attributes are displayed for which user feedback was received.

7. The method of claim 1, wherein the plurality of user instructions further includes at least one of: product type, product amount, dosage amount, concentration, batch, delivery method, administration time, and chemical data.

8. The method of claim 1, wherein the plurality of user instructions further includes at least one of: product type, product amount and dosage amount.

9. The method of claim 1, wherein the plurality of user instructions further includes at least one of: concentration, batch and chemical data.

10. The method of claim 1, wherein the plurality of user instructions further includes at least one of: delivery method and administration time.

11. A system for capturing user feedback, comprising:
a computing processor; and
a display interfaced with the computing processor,
wherein the computing processor is configured to:
receive a plurality of user instructions indicating (i) a symptom, condition or ailment, (ii) a score associated with the symptom, condition or ailment, and (iii) an indication of a session for treating the symptom, condition or ailment, and
receive user feedback comprising at least one of: an updated score and absence or presence of attributes;
execute a query on at least one of a memory internal to the computing processor and external to the computing processor to store the received user feedback,
repeat the receiving of user feedback and execution of the query, and
alert the user for input of user feedback after a predetermined period of time has elapsed following receipt of the user feedback without a subsequent receipt of user feedback, and
wherein the display, interfaced with the computing processor, is configured to display a scale associated with the score for use by the user of the computing processor to input user feedback including updated scores, wherein the scale incorporates a graphic user interface and is accompanied by a graphical display configured to update based on the updated score corresponding to a value of the graphic user interface.

12. The system of claim 11, wherein the computing processor is further configured to receive a user instruction indicating an ending of the session.

13. The system of claim 11, wherein
the plurality of user instructions further includes a product delivery method, and
the predetermined period of time is based on the product delivery method.

14. The system of claim 11, wherein the computing processing is configured to alert the user using at least one of: an audio emitting device configured to emit an audio signal and a display configured to display a message.

15. The system of claim 12, wherein
the display is configured to display a summary of the session after the ending of the session, wherein the summary includes a visual and/or written indication of the absence and presence of the plurality of attributes during the session based on the respective user feedback.

16. The system of claim 15, wherein the visual and/or written indication is displayed and only attributes are displayed for which user feedback was received.

17. The system of claim 11, wherein the plurality of user instructions further includes at least one of: product type, product amount, dosage amount, concentration, batch, delivery method, administration time, and chemical data.

18. The system of claim 11, wherein the plurality of user instructions further includes at least one of: product type, product amount, and dosage amount.

19. The system of claim 11, wherein the plurality of user instructions further includes at least one of: concentration, batch, and chemical data.

20. The system of claim 11, wherein the plurality of user instructions further includes at least one of: delivery method and administration time.

* * * * *